US010420830B2

(12) United States Patent
Ng et al.

(10) Patent No.: US 10,420,830 B2
(45) Date of Patent: Sep. 24, 2019

(54) NANOCAPSULES CARRYING CHIKUNGUNYA-ASSOCIATED PEPTIDES

(71) Applicants: AGENCY FOR SCIENCE, TECHNOLOGY AND RESEARCH, Singapore (SG); NANYANG TECHNOLOGICAL UNIVERSITY, Singapore (SG)

(72) Inventors: Fong Poh Lisa Ng, Singapore (SG); Yiu-Wing Jason Kam, Singapore (SG); Wei Ling Wendy Lee, Singapore (SG); Fok Moon Lum, Singapore (SG); Sierin Lim, Singapore (SG); Kang Yu, Singapore (SG); Chengxun Su, Singapore (SG)

(73) Assignees: AGENCY FOR SCIENCE, TECHNOLOGY AND RESEARCH, Singapore (SG); NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 15/547,476

(22) PCT Filed: Jan. 29, 2016

(86) PCT No.: PCT/SG2016/050046
§ 371 (c)(1),
(2) Date: Jul. 28, 2017

(87) PCT Pub. No.: WO2016/122414
PCT Pub. Date: Aug. 4, 2016

(65) Prior Publication Data
US 2018/0008690 A1 Jan. 11, 2018

(30) Foreign Application Priority Data
Jan. 29, 2015 (SG) ........................... 10201500725U

(51) Int. Cl.
| *A61K 39/12* | (2006.01) |
| *C07K 14/005* | (2006.01) |
| *C07K 14/18* | (2006.01) |
| *C07K 19/00* | (2006.01) |
| *A61K 9/51* | (2006.01) |
| *A61K 39/00* | (2006.01) |

(52) U.S. Cl.
CPC ............ *A61K 39/12* (2013.01); *A61K 9/5184* (2013.01); *C07K 14/005* (2013.01); *C07K 14/18* (2013.01); *C07K 19/00* (2013.01); *A61K 2039/55555* (2013.01); *A61K 2039/6031* (2013.01); *C07K 2319/00* (2013.01); *C12N 2770/36122* (2013.01); *C12N 2770/36134* (2013.01); *Y02A 50/383* (2018.01)

(58) Field of Classification Search
None
See application file for complete search history.

(56) References Cited

FOREIGN PATENT DOCUMENTS

| WO | WO 03/094849 A2 | 11/2003 |
| WO | WO 2006/074303 A2 | 7/2006 |
| WO | WO 2008/103920 A2 | 8/2008 |
| WO | WO 2009/051837 A2 | 4/2009 |
| WO | WO 2009/109426 A2 | 9/2009 |
| WO | WO 2012/078116 A1 * | 6/2012 |
| WO | WO 2012/162428 A1 | 11/2012 |
| WO | WO 2014/041189 A1 | 3/2014 |
| WO | WO 2014/049094 A1 * | 4/2014 |
| WO | WO 2014/160463 A1 | 10/2014 |
| WO | WO 2015/048149 A1 | 4/2015 |

OTHER PUBLICATIONS

Chen et al., Adv Drug Deliv Rev, 2013, 65(10):1357-1369. (Year: 2013).*
PCT International Search Report for PCT Counterpart Application No. PCT/SG2016/050046. 7 pgs. (dated Mar. 21, 2016).
PCT Written Opinion of the International Searching Authority for PCT Application No. PCT/SG2016/050046, 5 pgs. (dated Mar. 21, 2016).

* cited by examiner

*Primary Examiner* — Stacy B Chen
(74) *Attorney, Agent, or Firm* — Womble Bond Dickinson (US) LLP

(57) ABSTRACT

The present invention refers to a composition comprising a viral protein or fragment thereof, wherein the viral protein or fragment thereof is enclosed within a self-assembling protein nanocapsule, preferably ferritin, and wherein the viral protein, or fragment thereof is selected from a virus of the Togaviridae family. The viral protein or fragment thereof may also further be selected from a virus of the alphavirus subfamily.

18 Claims, 19 Drawing Sheets
Specification includes a Sequence Listing.

FIG. 8

```
GAGGAAGCCTCTGCCCTCGACATTGTGGAGAAGCTGAGGTTGATTGGAGA
||||||||||||||||||||||||||||||||||||||||||
GAGGAAGCCTCTGCCCTCGACATTGTGGAGAAGCTGAGGTTG---------

GGACGCGGCGGCTTTGCGGAGAGGACGCGGCGGCTTTGCTGGAGAGGACG

---------------------------------------------------

CGGCGGCTTTGCTTTTCATTGGAGAGGAC GCGGCG GCTTTGCTTTTCCTT
                 ||||||||||||| ||||| |||||||||||||||
-------------ATTGGAGAGGAC GCGGCG GCTTTGCTTTTCCTT

GATAAGGAGCTTTCTCTCAGGCAGTTTACTCCTCCAGCTGAGGAGGAGAA
||||||||||||||||||||||||||||||||||||||||||||||||||
GATAAGGAGCTTTCTCTCAGGCAGTTTACTCCTCCAGCTGAGGAGGAGAA

GTAAGGATCCGGATCGACGAGAGCAGCGCGACTGGATCTGTCGCCCGTCT
||||
GTAA----------------------------------------------
```

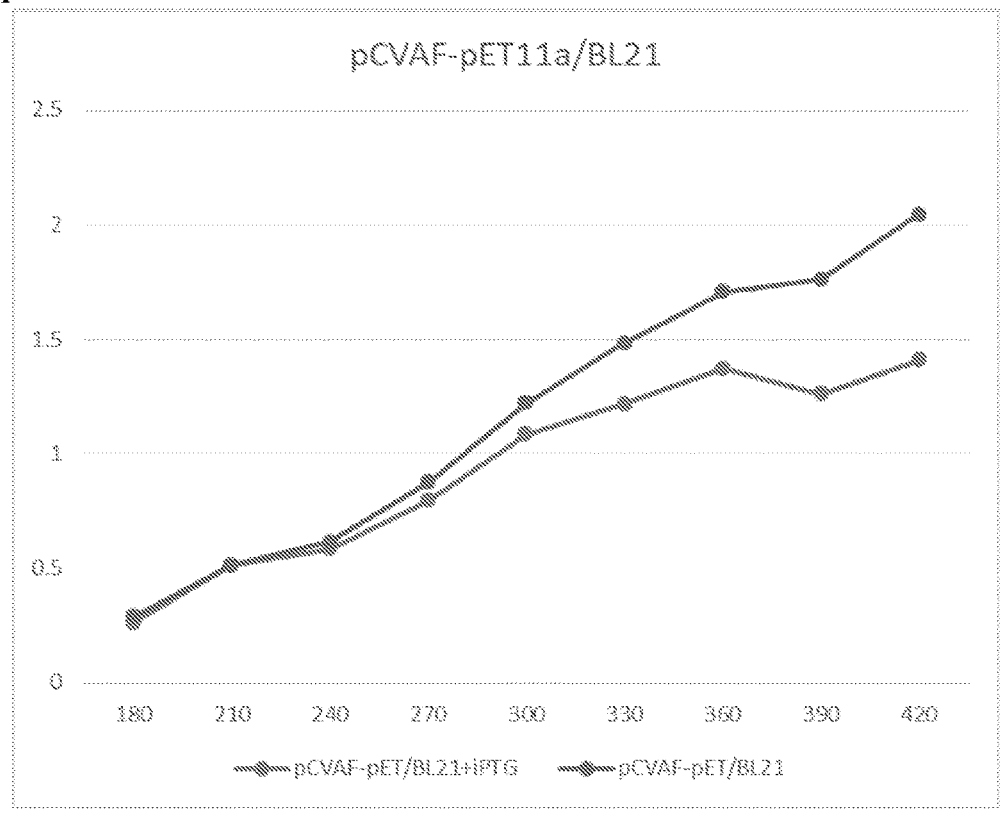

FIG. 9

FIG. 18
A
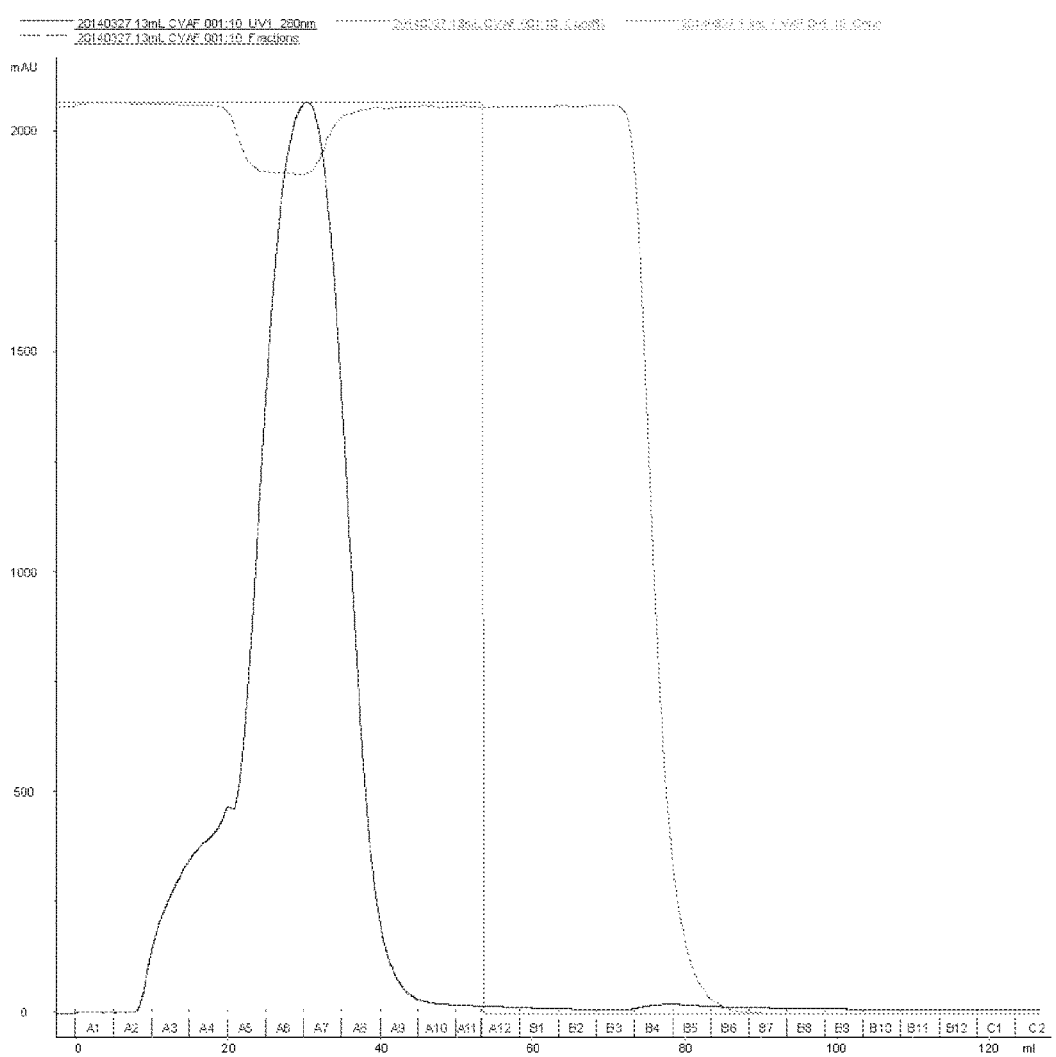
B
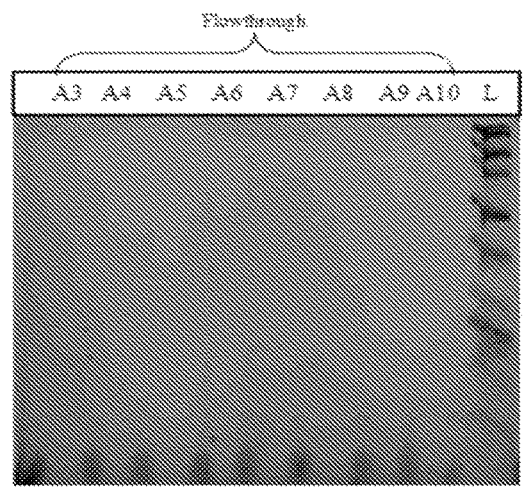

FIG. 19
A
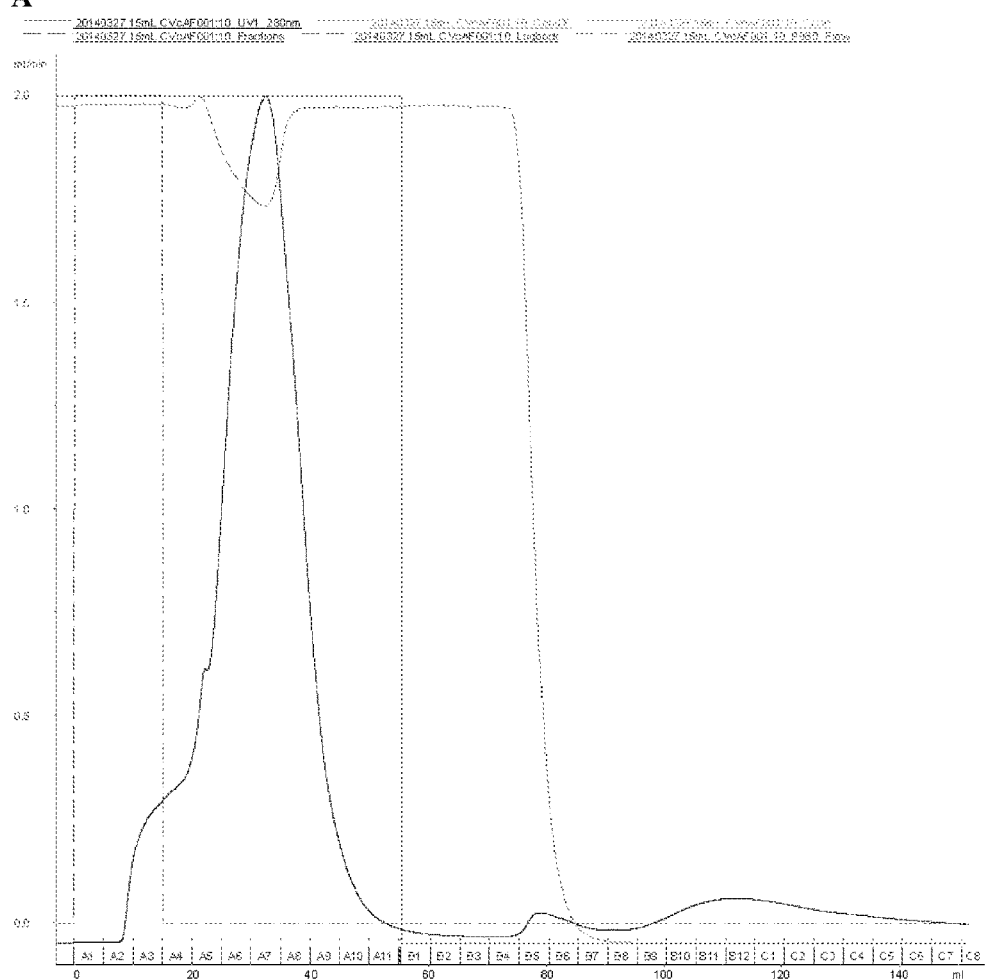
B
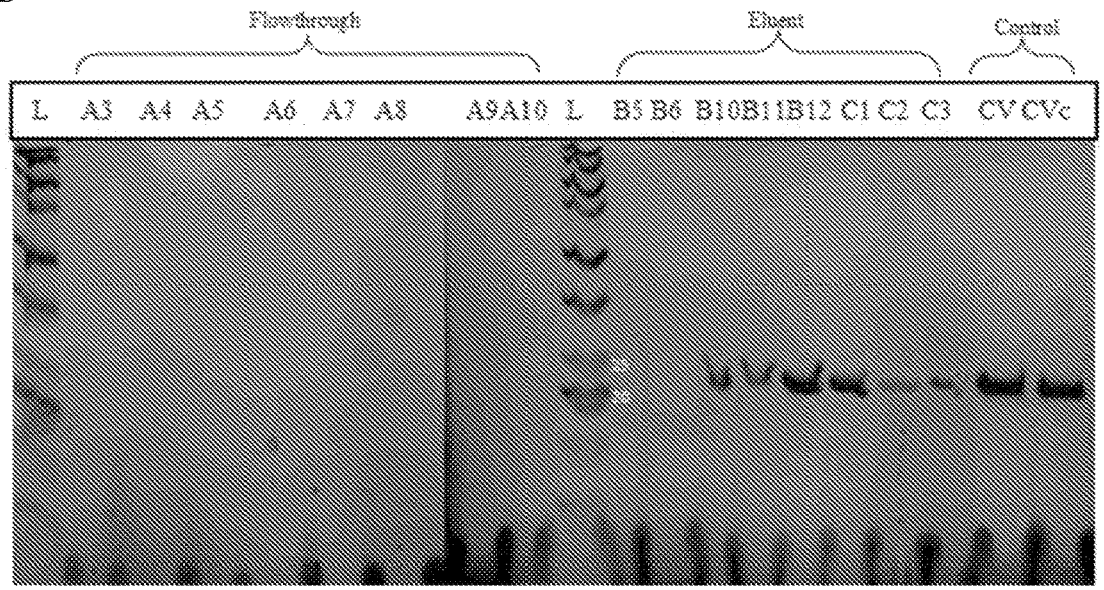

FIG. 20
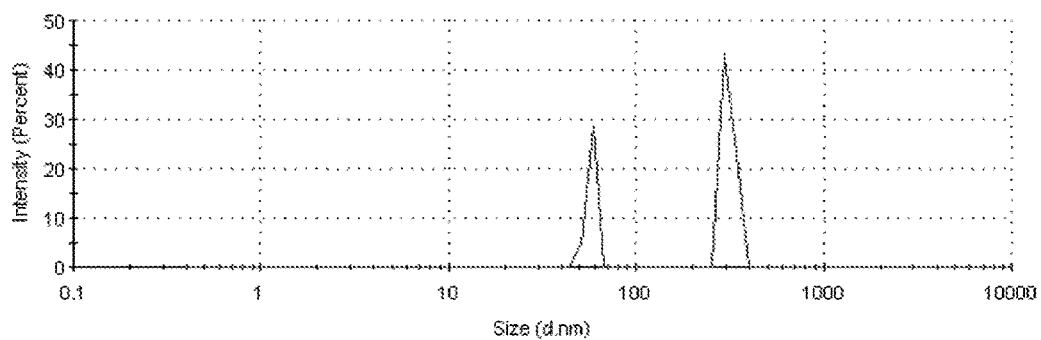
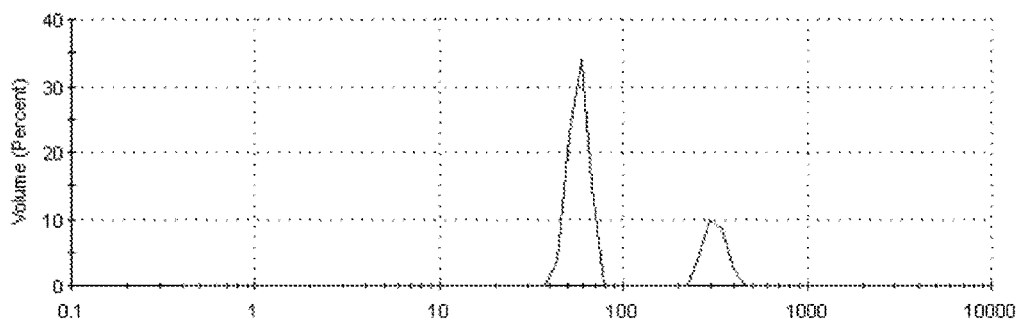

FIG. 21
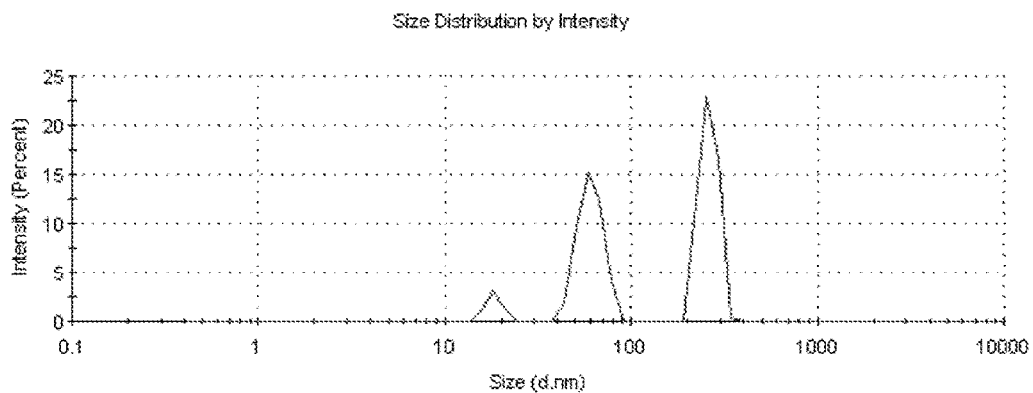
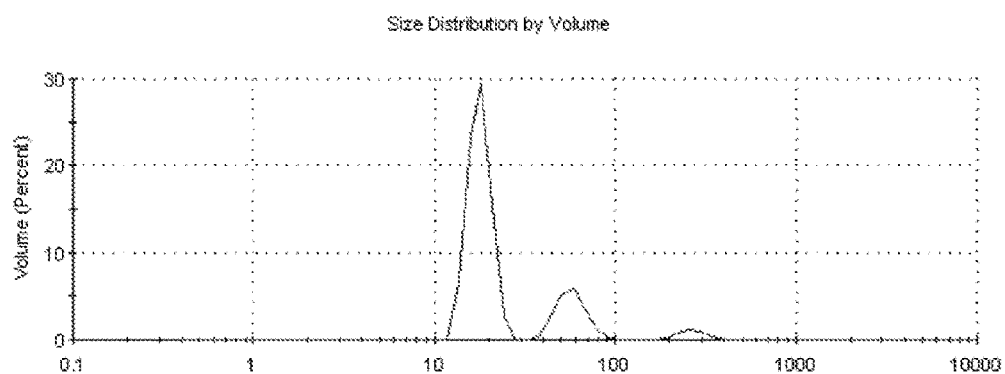

FIG. 22

```
result       751 CATATGAGCACCAAAGATAACTTTAATGTGTACAAAGCAACCCGTCCGTA
                 ||||||||||||||||||||||||||||||||||||||||||||||||||
theoretical    1 CATATGAGCACCAAAGATAACTTTAATGTGTACAAAGCAACCCGTCCGTA result       801 TCTGGCACATAGCGGTGGTGCTAGCATTTCTGAAAAAATGGTTGAGGCTT
                 ||||||||||||||||||||||||||||||||||||||||||||||||||
theoretical   51 TCTGGCACATAGCGGTGGTGCTAGCATTTCTGAAAAAATGGTTGAGGCTT result       851 TGAACAGGCAGATAAACGCTGAAATCTACTCAGCATACCTCTACCTCTCC
                 ||||||||||||||||||||||||||||||||||||||||||||||||||
theoretical  101 TGAACAGGCAGATAAACGCTGAAATCTACTCAGCATACCTCTACCTCTCC result       901 ATGGCCTCTTACTTCGACTCCATCGGGCTTAAGGGCTTCTCAAACTGGAT
                 ||||||||||||||||||||||||||||||||||||||||||||||||||
theoretical  151 ATGGCCTCTTACTTCGACTCCATCGGGCTTAAGGGCTTCTCAAACTGGAT result       951 GAGGGTGCAGTGGCAGGAGGAGCTGATGCATGCGATGAAGATGTTTGACT
                 ||||||||||||||||||||||||||||||||||||||||||||||||||
theoretical  201 GAGGGTGCAGTGGCAGGAGGAGCTGATGCATGCGATGAAGATGTTTGACT result      1001 TTGTCAGTGAGAGGGGAGGGAGAGTTAAGCTCTACGCTGTTGAGGAGCCA
                 ||||||||||||||||||||||||||||||||||||||||||||||||||
theoretical  251 TTGTCAGTGAGAGGGGAGGGAGAGTTAAGCTCTACGCTGTTGAGGAGCCA result      1051 CCATCTGAGTGGGATTCGCCTTTGGCAGCCTTTGAGCACGTTTACGAGCA
                 ||||||||||||||||||||||||||||||||||||||||||||||||||
theoretical  301 CCATCTGAGTGGGATTCGCCTTTGGCAGCCTTTGAGCACGTTTACGAGCA result      1101 TGAGGTAAATGTTACGAAGAGAATTCACGAGCTTGTTGAGATGGCAATGC
                 ||||||||||||||||||||||||||||||||||||||||||||||||||
theoretical  351 TGAGGTAAATGTTACGAAGAGAATTCACGAGCTTGTTGAGATGGCAATGC result      1151 AGGAAAAGGACTTTGCAACCTACAACTTCCTGCAGTGGTATGTTGCGGAG
                 ||||||||||||||||||||||||||||||||||||||||||||||||||
theoretical  401 AGGAAAAGGACTTTGCAACCTACAACTTCCTGCAGTGGTATGTTGCGGAG result      1201 CAGGTTGAGGAGGAAGCCTCTGCCCTCGACATTGTGGAGAAGCTGAGGTT
                 ||||||||||||||||||||||||||||||||||||||||||||||||||
theoretical  451 CAGGTTGAGGAGGAAGCCTCTGCCCTCGACATTGTGGAGAAGCTGAGGTT result      1251 GATTGGAGAGGACAAAAGGGCTTTGCTTTTCCTTGATAAGGAGCTTTCTC
                 ||||||||||||||||||||||||||||||||||||||||||||||||||
theoretical  501 GATTGGAGAGGACAAAAGGGCTTTGCTTTTCCTTGATAAGGAGCTTTCTC result      1301 TCAGGCAGTTTACTCCTCCAGCTGAGGAGGAGAAGTAAGGATCCGGATCG
                 |||||||||||||||||||||||||||||||||||||||||||||
theoretical  551 TCAGGCAGTTTACTCCTCCAGCTGAGGAGGAGAAGTAAGGATCC------
```

FIG. 23

```
result        151 CTCGCACCCATATGAGCACCAAAGATAACTTTAATGTGTACAAAAGCGGT
                          ||||||||||||||||||||||||||||||||||||||||||
theoretical     1 --------CATATGAGCACCAAAGATAACTTTAATGTGTACAAAAGCGGT result        201 GGTGCTAGCATTTCTGAAAAAATGGTTGAGGCTTTGAACAGGCAGATAAA
                  ||||||||||||||||||||||||||||||||||||||||||||||||||
theoretical    43 GGTGCTAGCATTTCTGAAAAAATGGTTGAGGCTTTGAACAGGCAGATAAA result        251 CGCTGAAATCTACTCAGCATACCTCTACCTCTCCATGGCCTCTTACTTCG
                  ||||||||||||||||||||||||||||||||||||||||||||||||||
theoretical    93 CGCTGAAATCTACTCAGCATACCTCTACCTCTCCATGGCCTCTTACTTCG result        301 ACTCCATCGGGCTTAAGGGCTTCTCAAACTGGATGAGGGTGCAGTGGCAG
                  ||||||||||||||||||||||||||||||||||||||||||||||||||
theoretical   143 ACTCCATCGGGCTTAAGGGCTTCTCAAACTGGATGAGGGTGCAGTGGCAG result        351 GAGGAGCTGATGCATGCGATGAAGATGTTTGACTTTGTCAGTGAGAGGGG
                  ||||||||||||||||||||||||||||||||||||||||||||||||||
theoretical   193 GAGGAGCTGATGCATGCGATGAAGATGTTTGACTTTGTCAGTGAGAGGGG result        401 AGGGAGAGTTAAGCTCTACGCTGTTGAGGAGCCACCATCTGAGTGGGATT
                  ||||||||||||||||||||||||||||||||||||||||||||||||||
theoretical   243 AGGGAGAGTTAAGCTCTACGCTGTTGAGGAGCCACCATCTGAGTGGGATT result        451 CGCCTTTGGCAGCCTTTGAGCACGTTTACGAGCATGAGGTAAATGTTACG
                  ||||||||||||||||||||||||||||||||||||||||||||||||||
theoretical   293 CGCCTTTGGCAGCCTTTGAGCACGTTTACGAGCATGAGGTAAATGTTACG result        501 AAGAGAATTCACGAGCTTGTTGAGATGGCAATGCAGGAAAAGGACTTTGC
                  ||||||||||||||||||||||||||||||||||||||||||||||||||
theoretical   343 AAGAGAATTCACGAGCTTGTTGAGATGGCAATGCAGGAAAAGGACTTTGC result        551 AACCTACAACTTCCTGCAGTGGTATGTTGCGGAGCAGGTTGAGGAGGAAG
                  ||||||||||||||||||||||||||||||||||||||||||||||||||
theoretical   393 AACCTACAACTTCCTGCAGTGGTATGTTGCGGAGCAGGTTGAGGAGGAAG result        601 CCTCTGCCCTCGACATTGTGGAGAAGCTGAGGTTGATTGGAGAGGACAAA
                  ||||||||||||||||||||||||||||||||||||||||||||||||||
theoretical   443 CCTCTGCCCTCGACATTGTGGAGAAGCTGAGGTTGATTGGAGAGGACAAA result        651 AGGGCTTTGCTTTTCCTTGATAAGGAGCTTTCTCTCAGGCAGTTTACTCC
                  ||||||||||||||||||||||||||||||||||||||||||||||||||
theoretical   493 AGGGCTTTGCTTTTCCTTGATAAGGAGCTTTCTCTCAGGCAGTTTACTCC result        701 TCCAGCTGAGGAGGAGAAGTAAGGATCCGGATCGACGAGAGCAGCGCGAC
                  |||||||||||||||||||||||||||||
theoretical   543 TCCAGCTGAGGAGGAGAAGTAAGGATCC---------------------
```

FIG. 24

| SEQ ID NO: | NAME (SEQUENCE TYPE) | SEQUENCE |
|---|---|---|
| 1 | E2EP3 (DNA) | AGCACCAAAGATAACTTTAATGTGTACAAAGCAACCCGTCCGTATCTGGCACAT |
| 2 | E2EP3 mutant (DNA) | AGTATTAAGGACCACTTCAATGTCTATAAAGCCACAAGACCGTACCTAGCTCAC |
| 3 | E2EP4 (DNA) | TGGGGCAACAACGAGCCGTATAAGTATTGGCCGCAGTTATCTACAAACGGTACA |
| 4 | E2EP5 (DNA) | CTCCTGTCGATGGTGGGTATGGCAGCGGGGATGTGCATGTGTGCACGACGCAGA |
| 5 | E2EP5 mutant (DNA) | CTCCTGTCGATGGTGGGTGTGGCAGTGGGGATGTGCATGTGTGCACGACGCAGA |
| 6 | CV (DNA) | AGCACCAAAGATAACTTTAATGTGTACAAA |
| 7 | E2EP3 (protein) | STKDNFNVYKATRPYLAH |
| 8 | E2EP3 mutant (protein) | SIKDHFNVYKATRPYLAH |
| 9 | E2EP4 (protein) | WGNNEPYKYWPQLSTNGT |
| 10 | E2EP5 (protein) | LLSMVGMAAGMCMCARRR |
| 11 | E2EP5 mutant (protein) | LLSMVGVAVGMCMCARRRK |
| 12 | CV (protein) | STKDNFNVYK |
| 13 | Mutated ferritin (DNA) | ATGGCATCCATTTCTGAAAAAATGGTTGAGGCTTTGAACAGGCAGATAAACGCTGAAATCTACTCAGCATACCTCTACCTCTCCATGGCCTCTTACTTCGACTCCATCGGGCTTAAGGGCTTCTCAAACTGGATGAGGGTGCAGTGGCAGGAGGAGCTGATGCATGCGATGAAGATGTTTGACTTTGTCAGTGAGAGGGGAGGGAGAGTTAAGCTCTACGCTGTTGAGGAGCCACCATCTGAGTGGGATTCGCCTTTGGCAGCCTTTGAGCACGTTTACGAGCATGAGGTAAATGTTACGAAGAGAATTCACGAGCTTGTTGAGATGGCAATGCAGGAAAAGGACTTTGCAACCTACAACTTCCTGCAGTGGTATGTTGCGGAGCAGGTTGAGGAGGAAGCCTCTGCCCTCGACATTGTGGAGAAGCTGAGGTTGATTGGAGAGGACGCGGCGGCTTTGCTTTTCCTTGATAAGGAGCTTTCTCTCAGGCAGTTTACTCCTCCAGCTGAGGAGGAGAAGTAATGA |

FIG. 24 continued

| SEQ ID NO: | NAME (SEQUENCE TYPE) | SEQUENCE |
|---|---|---|
| 14 | Mutated ferritin (protein) | MASISEKMVEALNRQINAEIYSAYLYLSMASYFDSIGLK GFSNWMRVQWQEELMHAMKMF DFVSERGGRVKLYAVEEPPSEWDSPLAAFEHVYEHEVN VTKRIHELVEMAMQEKDFATYN FLQWYVAEQVEEEASALDIVEKLRLIGEDAAALLFLDK ELSLRQFTPPAEEEK** |
| 15 | Wild type ferritin (DNA) | ATGGCATCCATTTCTGAAAAAATGGTTGAGGCTTTGA ACAGGCAGATAAACGCTGAAATC TACTCAGCATACCTCTACCTCTCCATGGCCTCTTACTT CGACTCCATCGGGCTTAAGGGC TTCTCAAACTGGATGAGGGTGCAGTGGCAGGAGGAG CTGATGCATGCGATGAAGATGTTT GACTTTGTCAGTGAGAGGGGAGGGAGAGTTAAGCTC TACGCTGTTGAGGAGCCACCATCT GAGTGGGATTCGCCTTTGGCAGCCTTTGAGCACGTTT ACGAGCATGAGGTAAATGTTACG AAGAGAATTCACGAGCTTGTTGAGATGGCAATGCAG GAAAAGGACTTTGCAACCTACAAC TTCCTGCAGTGGTATGTTGCGGAGCAGGTTGAGGAGG AAGCCTCTGCCCTCGACATTGTG GAGAAGCTGAGGTTGATTGGAGAGGACAAAAGGGCT TTGCTTTTCCTTGATAAGGAGCTT TCTCTCAGGCAGTTTACTCCTCCAGCTGAGGAGGAGA AGTAATGA |
| 16 | Wild type ferritin (protein) | MASISEKMVEALNRQINAEIYSAYLYLSMASYFDSIGLK GFSNWMRVQWQEELMHAMKMF DFVSERGGRVKLYAVEEPPSEWDSPLAAFEHVYEHEVN VTKRIHELVEMAMQEKDFATYN FLQWYVAEQVEEEASALDIVEKLRLIGEDKRALLFLDK ELSLRQFTPPAEEEK** |
| 17 | Mutagenesis primer forward | gattggagaggacGCGGCGgctttgcttttc |
| 18 | Mutagenesis primer reverse | gaaaagcaaagcCGCCGCgtcctctccaatc |
| 19 | CVAf (protein) | STKDNFNVYKATRPYLAHSGGASISEKMVEALNRQINA EIYSAYLYLSMASYFDSIGLKGFSNWMRVQWQEELMH AMKMFDFVSERGGRVKLYAVEEPPSEWDSPLAAFEHV YEHEVNVTKRIHELVEMAMQEKDFATYNFLQWYVAEQ VEEEASALDIVEKLRLIGEDKRALLFLDKELSLRQFTPPA EEEK |
| 20 | CVcAf (protein) | STKDNFNVYKSGGASISEKMVEALNRQINAEIYSAYLYL SMASYFDSIGLKGFSNWMRVQWQEELMHAMKMFDFV SERGGRVKLYAVEEPPSEWDSPLAAFEHVYEHEVNVTK RIHELVEMAMQEKDFATYNFLQWYVAEQVEEEASALD IVEKLRLIGEDKRALLFLDKELSLRQFTPPAEEEK |

SEQUENCE LISTING

<160> NUMBER OF SEQ ID NOS: 26

<210> SEQ ID NO 1
<211> LENGTH: 54
<212> TYPE: DNA
<213> ORGANISM: Artificial
<220> FEATURE:
<223> OTHER INFORMATION: E2EP3

<400> SEQUENCE: 1
agcaccaaag ataactttaa tgtgtacaaa gcaaccgtc cgtatctggc acat      54

```
<210> SEQ ID NO 2
<211> LENGTH: 54
<212> TYPE: DNA
<213> ORGANISM: Artificial
<220> FEATURE:
<223> OTHER INFORMATION: E2EP3 mutant

<400> SEQUENCE: 2
agtattaagg accacttcaa tgtctataaa gccacaagac cgtacctagc tcac          54

<210> SEQ ID NO 3
<211> LENGTH: 54
<212> TYPE: DNA
<213> ORGANISM: Artificial
<220> FEATURE:
<223> OTHER INFORMATION: E2EP4

<400> SEQUENCE: 3
tggggcaaca acgagccgta taagtattgg ccgcagttat ctacaaacgg taca          54

<210> SEQ ID NO 4
<211> LENGTH: 54
<212> TYPE: DNA
<213> ORGANISM: Artificial
<220> FEATURE:
<223> OTHER INFORMATION: E2EP5

<400> SEQUENCE: 4
ctcctgtcga tggtgggtat ggcagcgggg atgtgcatgt gtgcacgacg caga          54

<210> SEQ ID NO 5
<211> LENGTH: 54
<212> TYPE: DNA
<213> ORGANISM: artificial
<220> FEATURE:
<223> OTHER INFORMATION: E2EP5 mutant

<400> SEQUENCE: 5
ctcctgtcga tggtgggtgt ggcagtgggg atgtgcatgt gtgcacgacg caga          54

<210> SEQ ID NO 6
<211> LENGTH: 30
<212> TYPE: DNA
<213> ORGANISM: artificial
<220> FEATURE:
<223> OTHER INFORMATION: E2EP3 CV

<400> SEQUENCE: 6
agcaccaaag ataactttaa tgtgtacaaa                                     30

<210> SEQ ID NO 7
<211> LENGTH: 18
<212> TYPE: PRT
<213> ORGANISM: artificial
<220> FEATURE:
<223> OTHER INFORMATION: E2EP3

<400> SEQUENCE: 7

Ser Thr Lys Asp Asn Phe Asn Val Tyr Lys Ala Thr Arg Pro Tyr Leu
1               5                   10                  15

Ala His

<210> SEQ ID NO 8
<211> LENGTH: 18
<212> TYPE: PRT
```

<213> ORGANISM: artificial
<220> FEATURE:
<223> OTHER INFORMATION: E2EP3 mutant

<400> SEQUENCE: 8

Ser Ile Lys Asp His Phe Asn Val Tyr Lys Ala Thr Arg Pro Tyr Leu
1               5                   10                  15
Ala His

<210> SEQ ID NO 9
<211> LENGTH: 18
<212> TYPE: PRT
<213> ORGANISM: Artificial
<220> FEATURE:
<223> OTHER INFORMATION: E2EP4

<400> SEQUENCE: 9

Trp Gly Asn Asn Glu Pro Tyr Lys Tyr Trp Pro Gln Leu Ser Thr Asn
1               5                   10                  15
Gly Thr

<210> SEQ ID NO 10
<211> LENGTH: 18
<212> TYPE: PRT
<213> ORGANISM: artificial
<220> FEATURE:
<223> OTHER INFORMATION: E2EP5

<400> SEQUENCE: 10

Leu Leu Ser Met Val Gly Met Ala Ala Gly Met Cys Met Cys Ala Arg
1               5                   10                  15
Arg Arg

<210> SEQ ID NO 11
<211> LENGTH: 19
<212> TYPE: PRT
<213> ORGANISM: artificial
<220> FEATURE:
<223> OTHER INFORMATION: E2EP5 mutant

<400> SEQUENCE: 11

Leu Leu Ser Met Val Gly Val Ala Val Gly Met Cys Met Cys Ala Arg
1               5                   10                  15
Arg Arg Lys

<210> SEQ ID NO 12
<211> LENGTH: 10
<212> TYPE: PRT
<213> ORGANISM: artificial
<220> FEATURE:
<223> OTHER INFORMATION: E2EP3 CV

<400> SEQUENCE: 12

Ser Thr Lys Asp Asn Phe Asn Val Tyr Lys
1               5                   10

<210> SEQ ID NO 13
<211> LENGTH: 525
<212> TYPE: DNA
<213> ORGANISM: artificial
<220> FEATURE:
<223> OTHER INFORMATION: Mutated ferritin

<400> SEQUENCE: 13

```
atggcatcca tttctgaaaa aatggttgag ctttgaaca ggcagataaa cgctgaaatc      60
tactcagcat acctctacct ctccatggcc tcttacttcg actccatcgg cttaagggc    120 ttctcaaact ggatgagggt gcagtggcag gaggagctga tgcatgcgat gaagatgttt    180
gactttgtca gtgagagggg agggagagtt aagctctacg ctgttgagga gccaccatct    240
gagtgggatt cgcctttggc agcctttgag cacgtttacg agcatgaggt aaatgttacg    300
aagagaattc acgagcttgt tgagatggca atgcaggaaa aggactttgc aacctacaac    360
ttcctgcagt ggtatgttgc ggagcaggtt gaggaggaag cctctgccct cgacattgtg    420
gagaagctga ggttgattgg agaggacgcg gcggctttgc ttttccttga taaggagctt    480
tctctcaggc agtttactcc tccagctgag gaggagaagt aatga                   525
```

<210> SEQ ID NO 14
<211> LENGTH: 173
<212> TYPE: PRT
<213> ORGANISM: artificial
<220> FEATURE:
<223> OTHER INFORMATION: Mutated ferritin

<400> SEQUENCE: 14

```
Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Glu
        115                 120                 125

Gln Val Glu Glu Glu Ala Ser Ala Leu Asp Ile Val Glu Lys Leu Arg
    130                 135                 140

Leu Ile Gly Glu Asp Ala Ala Ala Leu Leu Phe Leu Asp Lys Glu Leu
145                 150                 155                 160

Ser Leu Arg Gln Phe Thr Pro Pro Ala Glu Glu Glu Lys
                165                 170
```

<210> SEQ ID NO 15
<211> LENGTH: 525
<212> TYPE: DNA
<213> ORGANISM: artificial
<220> FEATURE:
<223> OTHER INFORMATION: Wild type ferritin

<400> SEQUENCE: 15

```
atggcatcca tttctgaaaa aatggttgag ctttgaaca ggcagataaa cgctgaaatc      60
tactcagcat acctctacct ctccatggcc tcttacttcg actccatcgg cttaagggc    120 ttctcaaact ggatgagggt gcagtggcag gaggagctga tgcatgcgat gaagatgttt    180
gactttgtca gtgagagggg agggagagtt aagctctacg ctgttgagga gccaccatct    240
```

```
gagtgggatt cgcctttggc agcctttgag cacgtttacg agcatgaggt aaatgttacg      300
aagagaattc acgagcttgt tgagatggca atgcaggaaa aggactttgc aacctacaac      360
ttcctgcagt ggtatgttgc ggagcaggtt gaggaggaag cctctgccct cgacattgtg      420
gagaagctga ggttgattgg agaggacaaa agggctttgc ttttccttga taaggagctt      480
tctctcaggc agtttactcc tccagctgag gaggagaagt aatga                     525
```

```
<210> SEQ ID NO 16
<211> LENGTH: 173
<212> TYPE: PRT
<213> ORGANISM: artificial
<220> FEATURE:
<223> OTHER INFORMATION: Wild type ferritin

<400> SEQUENCE: 16
```

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Glu
        115                 120                 125

Gln Val Glu Glu Glu Ala Ser Ala Leu Asp Ile Val Glu Lys Leu Arg
    130                 135                 140

Leu Ile Gly Glu Asp Lys Arg Ala Leu Leu Phe Leu Asp Lys Glu Leu
145                 150                 155                 160

Ser Leu Arg Gln Phe Thr Pro Pro Ala Glu Glu Glu Lys
                165                 170

```
<210> SEQ ID NO 17
<211> LENGTH: 31
<212> TYPE: DNA
<213> ORGANISM: artificial
<220> FEATURE:
<223> OTHER INFORMATION: Mutagenesis primer (forward)

<400> SEQUENCE: 17
gattggagag gacgcggcgg ctttgctttt c                                    31

<210> SEQ ID NO 18
<211> LENGTH: 31
<212> TYPE: DNA
<213> ORGANISM: artificial
<220> FEATURE:
<223> OTHER INFORMATION: Mutagenesis primer (reverse)

<400> SEQUENCE: 18
gaaaagcaaa gccgccgcgt cctctccaat c                                    31

<210> SEQ ID NO 19
```

<211> LENGTH: 193
<212> TYPE: PRT
<213> ORGANISM: artificial
<220> FEATURE:
<223> OTHER INFORMATION: CVAf

<400> SEQUENCE: 19

Ser Thr Lys Asp Asn Phe Asn Val Tyr Lys Ala Thr Arg Pro Tyr Leu
1               5                   10                  15

Ala His Ser Gly Gly Ala Ser Ile Ser Glu Lys Met Val Glu Ala Leu
            20                  25                  30

Asn Arg Gln Ile Asn Ala Glu Ile Tyr Ser Ala Tyr Leu Tyr Leu Ser
        35                  40                  45

Met Ala Ser Tyr Phe Asp Ser Ile Gly Leu Lys Gly Phe Ser Asn Trp
    50                  55                  60

Met Arg Val Gln Trp Gln Glu Leu Met His Ala Met Lys Met Phe
65                  70                  75                  80

Asp Phe Val Ser Glu Arg Gly Gly Arg Val Lys Leu Tyr Ala Val Glu
                85                  90                  95

Glu Pro Pro Ser Glu Trp Asp Ser Pro Leu Ala Ala Phe Glu His Val
            100                 105                 110

Tyr Glu His Glu Val Asn Val Thr Lys Arg Ile His Glu Leu Val Glu
        115                 120                 125

Met Ala Met Gln Glu Lys Asp Phe Ala Thr Tyr Asn Phe Leu Gln Trp
    130                 135                 140

Tyr Val Ala Glu Gln Val Glu Glu Ala Ser Ala Leu Asp Ile Val
145                 150                 155                 160

Glu Lys Leu Arg Leu Ile Gly Glu Asp Lys Arg Ala Leu Leu Phe Leu
                165                 170                 175

Asp Lys Glu Leu Ser Leu Arg Gln Phe Thr Pro Pro Ala Glu Glu Glu
            180                 185                 190

Lys

<210> SEQ ID NO 20
<211> LENGTH: 185
<212> TYPE: PRT
<213> ORGANISM: artificial
<220> FEATURE:
<223> OTHER INFORMATION: CVcAf

<400> SEQUENCE: 20

Ser Thr Lys Asp Asn Phe Asn Val Tyr Lys Ser Gly Gly Ala Ser Ile
1               5                   10                  15

Ser Glu Lys Met Val Glu Ala Leu Asn Arg Gln Ile Asn Ala Glu Ile
            20                  25                  30

Tyr Ser Ala Tyr Leu Tyr Leu Ser Met Ala Ser Tyr Phe Asp Ser Ile
        35                  40                  45

Gly Leu Lys Gly Phe Ser Asn Trp Met Arg Val Gln Trp Gln Glu Glu
    50                  55                  60

Leu Met His Ala Met Lys Met Phe Asp Phe Val Ser Glu Arg Gly Gly
65                  70                  75                  80

Arg Val Lys Leu Tyr Ala Val Glu Glu Pro Pro Ser Glu Trp Asp Ser
                85                  90                  95

Pro Leu Ala Ala Phe Glu His Val Tyr Glu His Glu Val Asn Val Thr
            100                 105                 110

Lys Arg Ile His Glu Leu Val Glu Met Ala Met Gln Glu Lys Asp Phe
        115                 120                 125

```
Ala Thr Tyr Asn Phe Leu Gln Trp Tyr Val Ala Glu Gln Val Glu Glu
    130                 135                 140

Glu Ala Ser Ala Leu Asp Ile Val Glu Lys Leu Arg Leu Ile Gly Glu
145                 150                 155                 160

Asp Lys Arg Ala Leu Leu Phe Leu Asp Lys Glu Leu Ser Leu Arg Gln
                165                 170                 175

Phe Thr Pro Pro Ala Glu Glu Glu Lys
            180                 185

<210> SEQ ID NO 21
<211> LENGTH: 250
<212> TYPE: DNA
<213> ORGANISM: Artificial sequence
<220> FEATURE:
<223> OTHER INFORMATION: Sequencing result of theoretical DNA sequence
      of pCVAf after site-directed mutagenesis (top line; Figure 8)

<400> SEQUENCE: 21
gaggaagcct ctgccctcga cattgtggag aagctgaggt tgattggaga ggacgcggcg      60
gctttgcgga gaggacgcgg cggctttgct ggagaggacg cggcggcttt gcttttcatt    120
ggagaggacg cggcggcttt gcttttcctt gataaggagc tttctctcag gcagtttact    180
cctccagctg aggaggagaa gtaaggatcc ggatcgacga gagcagcgcg actggatctg    240
tcgcccgtct                                                           250

<210> SEQ ID NO 22
<211> LENGTH: 129
<212> TYPE: DNA
<213> ORGANISM: Artificial sequence
<220> FEATURE:
<223> OTHER INFORMATION: theoretical DNA sequence of pCVAf after site-
      directed mutagenesis (bottom line; Fig. 8)

<400> SEQUENCE: 22
gaggaagcct ctgccctcga cattgtggag aagctgaggt tgattggaga ggacgcggcg      60
gctttgcttt tccttgataa ggagctttct ctcaggcagt ttactcctcc agctgaggag    120
gagaagtaa                                                            129

<210> SEQ ID NO 23
<211> LENGTH: 600
<212> TYPE: DNA
<213> ORGANISM: Artificial sequence
<220> FEATURE:
<223> OTHER INFORMATION: sequence alignment comparison for pCVAf-pET-11a
      (result)

<400> SEQUENCE: 23
catatgagca ccaaagataa ctttaatgtg tacaaagcaa cccgtccgta tctggcacat      60
agcggtggtg ctagcatttc tgaaaaaatg gttgaggctt tgaacaggca gataaacgct    120
gaaatctact cagcatacct ctacctctcc atggcctctt acttcgactc catcgggctt    180
aagggcttct caaactggat gagggtgcag tggcaggagg agctgatgca tgcgatgaag    240
atgtttgact tgtcagtga gaggggaggg agagttaagc tctacgctgt tgaggagcca    300
ccatctgagt gggattcgcc tttggcagcc tttgagcacg tttacgagca tgaggtaaat    360
gttacgaaga gaattcacga gcttgttgag atggcaatgc aggaaaagga ctttgcaacc    420
tacaacttcc tgcagtggta tgttgcggag caggttgagg aggaagcctc tgccctcgac    480
attgtggaga agctgaggtt gattggagag gacaaaaggg ctttgctttt ccttgataag    540
```
gagctttctc tcaggcagtt tactcctcca gctgaggagg agaagtaagg atccggatcg    600

<210> SEQ ID NO 24
<211> LENGTH: 594
<212> TYPE: DNA
<213> ORGANISM: Artificial sequence
<220> FEATURE:
<223> OTHER INFORMATION: sequence alignment comparison for pCVAf-pET-11a
      (theoretical; Fig. 22)

<400> SEQUENCE: 24
catatgagca ccaaagataa ctttaatgtg tacaaagcaa cccgtccgta tctggcacat     60
agcggtggtg ctagcatttc tgaaaaaatg gttgaggctt tgaacaggca gataaacgct    120
gaaatctact cagcatacct ctacctctcc atggcctctt acttcgactc catcgggctt    180
aagggcttct caaactggat gagggtgcag tggcaggagg agctgatgca tgcgatgaag    240
atgtttgact ttgtcagtga gggggaggg agagttaagc tctacgctgt tgaggagcca    300
ccatctgagt gggattcgcc tttggcagcc tttgagcacg tttacgagca tgaggtaaat    360
gttacgaaga gaattcacga gcttgttgag atggcaatgc aggaaaagga ctttgcaacc    420
tacaacttcc tgcagtggta tgttgcggag caggttgagg aggaagcctc tgccctcgac    480
attgtggaga agctgaggtt gattggagag acaaaaggg ctttgctttt ccttgataag    540
gagctttctc tcaggcagtt tactcctcca gctgaggagg agaagtaagg atcc          594

<210> SEQ ID NO 25
<211> LENGTH: 600
<212> TYPE: DNA
<213> ORGANISM: Artificial sequence
<220> FEATURE:
<223> OTHER INFORMATION: sequence alignment comparison for pCVAf-pET-11a
      (results; Fig. 23)

<400> SEQUENCE: 25
ctcgcaccca tatgagcacc aaagataact ttaatgtgta caaaagcggt ggtgctagca     60
tttctgaaaa aatggttgag ctttgaaca ggcagataaa cgctgaaatc tactcagcat    120
acctctacct ctccatggcc tcttacttcg actccatcgg gcttaagggc ttctcaaact    180
ggatgagggt gcagtggcag gaggagctga tgcatgcgat gaagatgttt gactttgtca    240
gtgagagggg agggagagtt aagctctacg ctgttgagga gccaccatct gagtgggatt    300
cgcctttggc agcctttgag cacgtttacg agcatgaggt aaatgttacg aagagaattc    360
acgagcttgt tgagatggca atgcaggaaa aggactttgc aacctacaac ttcctgcagt    420
ggtatgttgc ggagcaggtt gaggaggaag cctctgccct cgacattgtg gagaagctga    480
ggttgattgg agaggacaaa agggctttgc ttttccttga taaggagctt tctctcaggc    540
agtttactcc tccagctgag gaggagaagt aaggatccgg atcgacgaga gcagcgcgac    600

<210> SEQ ID NO 26
<211> LENGTH: 570
<212> TYPE: DNA
<213> ORGANISM: Artificial sequence
<220> FEATURE:
<223> OTHER INFORMATION: sequence alignment comparison for pCVcAf-pET-
      11a (theoretical)

<400> SEQUENCE: 26
catatgagca ccaaagataa ctttaatgtg tacaaaagcg gtggtgctag catttctgaa     60
aaaatggttg aggctttgaa caggcagata aacgctgaaa tctactcagc atacctctac    120

-continued

```
ctctccatgg cctcttactt cgactccatc gggcttaagg gcttctcaaa ctggatgagg    180
gtgcagtggc aggaggagct gatgcatgcg atgaagatgt ttgactttgt cagtgagagg    240
ggagggagag ttaagctcta cgctgttgag gagccaccat ctgagtggga ttcgcctttg    300
gcagcctttg agcacgttta cgagcatgag gtaaatgtta cgaagagaat tcacgagctt    360
gttgagatgg caatgcagga aaaggacttt gcaacctaca acttcctgca gtggtatgtt    420
gcggagcagg ttgaggagga agcctctgcc ctcgacattg tggagaagct gaggttgatt    480
ggagaggaca aagggctttt gcttttcctt gataaggagc tttctctcag gcagtttact    540
cctccagctg aggaggagaa gtaaggatcc                                      570
```

NANOCAPSULES CARRYING CHIKUNGUNYA-ASSOCIATED PEPTIDES

CROSS-REFERENCE TO RELATED APPLICATIONS

This patent application is a U.S. National Phase Application under 35 U.S.C. § 371 of International Application No. PCT/SG2016/050046, filed on 29 Jan. 2016, entitled NANOCAPSULES CARRYING CHIKUNGUNYA-ASSOCIATED PEPTIDES, which claims the benefit of priority of Singapore Patent Application No. 10201500725U, filed on 29 Jan. 2015, the content of which was incorporated by reference in its entirety for all purposes.

INCORPORATION BY REFERENCE

This patent application incorporates by reference the material (i.e., Sequence Listing) in the ASCII text file named 9869SG3612 includes SEQ from FIGS. 8 22 and 23_ST25.txt, created on Dec. 12, 2017, having a file size of 16,364 bytes, and the ASCII text filed named 9869SG3612_ST25_3375411_2.txt, created on Feb. 28, 2019, having a file size of 16,104 bytes.

FIELD OF THE INVENTION

The present invention relates generally to the field of nanotechnology. In particular, the present invention relates to nanocapsules for peptide delivery.

BACKGROUND OF THE INVENTION

Chikungunya virus (CHIKV) is a human pathogen and one of the leading causes of mosquito-borne arthralgia in parts of Africa, India and Southeast Asia. The disease of the same name, Chikungunya is a transmitted by Chikungunya virus (CHIKV)-carrying Aedes mosquitoes. Since Chikungunya symptoms are very similar to Dengue fever, it is often misdiagnosed. In the year 2006, total number of 1,390,322 suspected Chikungunya fever cases was reported in India. The disease was unknown in Singapore until 2008, when it experienced its first successive waves of Chikungunya fever. According to Singapore Ministry of Health and The Strait Times, the total number of infections in the last five years is about 1500. With no specific treatment or any licensed vaccine to prevent Chikungunya, the disease remains a public health threat.

Therefore, there is a need to develop an effective vaccine against the disease caused by the Chikungunya virus.

SUMMARY

In one aspect, the present invention refers to a composition comprising a viral protein or fragment thereof, wherein the viral protein, or fragment thereof is enclosed within a nanocapsule, and wherein the viral protein, or fragment thereof is selected from a virus of the Togaviridae family.

In one aspect, the present invention refers to a method of eliciting an immune response in a subject, the method comprising administering to the subject the composition as described herein.

In another aspect, the present invention refers to a vaccine for use preventing an infection caused by an agent selected from the group consisting of Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus Chikungunya virus, O'nyong'nyong virus, Semliki Forest virus, Sindbis virus, and Ross River virus, the vaccine comprising the composition as described herein.

In yet another aspect, the present invention refers to a method of preventing or ameliorating an infection caused by an agent selected from the group consisting of Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus Chikungunya virus, O'nyong'nyong virus, Semliki Forest virus, Sindbis virus and Ross River virus, the method comprising administering to a subject the composition as described herein.

In a further aspect, the present invention refers to a nucleic acid sequence comprising a gene encoding the viral protein or fragment thereof as described herein, the linker sequence as described herein and the scaffold protein as described herein.

In yet a further aspect, the present invention refers to a vector comprising the nucleic acid sequence as described herein.

In one aspect, the present invention refers to an isolated host cell comprising the vector as described herein.

In another aspect, the present invention refers to a method of producing the composition as described herein, the method comprising isolating the protein expressed by the vector as described herein, and adding a catalyst in an amount sufficient to catalyse the formation of the nanocapsule.

BRIEF DESCRIPTION OF THE DRAWINGS

The invention will be better understood with reference to the detailed description when considered in conjunction with the non-limiting examples and the accompanying drawings, in which.

mutant (AfFtn-AA) *Archaeoglobulus fulgidus* ferritins, respectively. Wild type ferritin (AfFtn; SEQ ID NO: 15 or SEQ ID NO: 16) has a unique tetracosameric structure with triangular opening (~45 Å in diameter) for every six subunits, while the mutated ferritin AfFtn-AA is a mutated protein from the wild type where amino acid residues Lysine at site 150 and Arginine at site 151 were both replaced with Alanine. As a result of mutation, the AfFtn-AA has a closed spherical structure.

Figure 4:
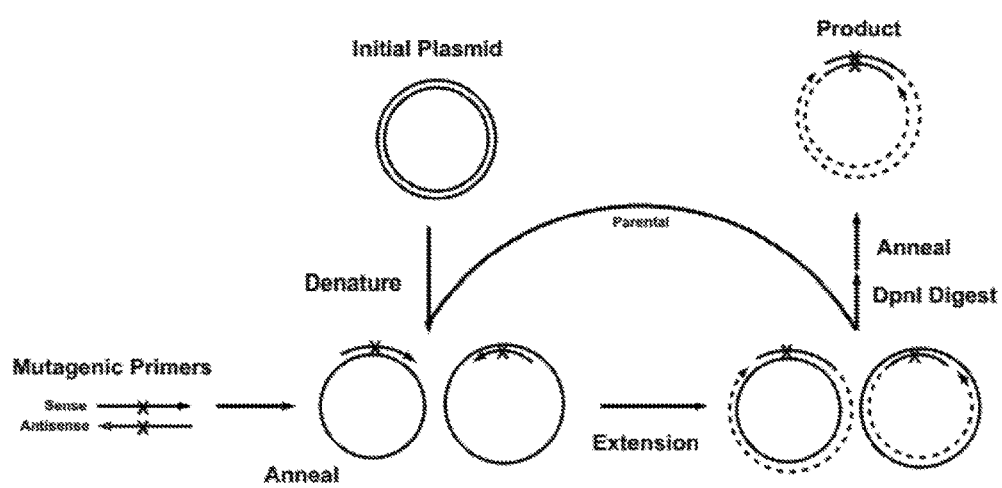

FIG. 4 shows a general schematic outlining the mechanism underlying site-directed mutagenesis.

Figure 5:
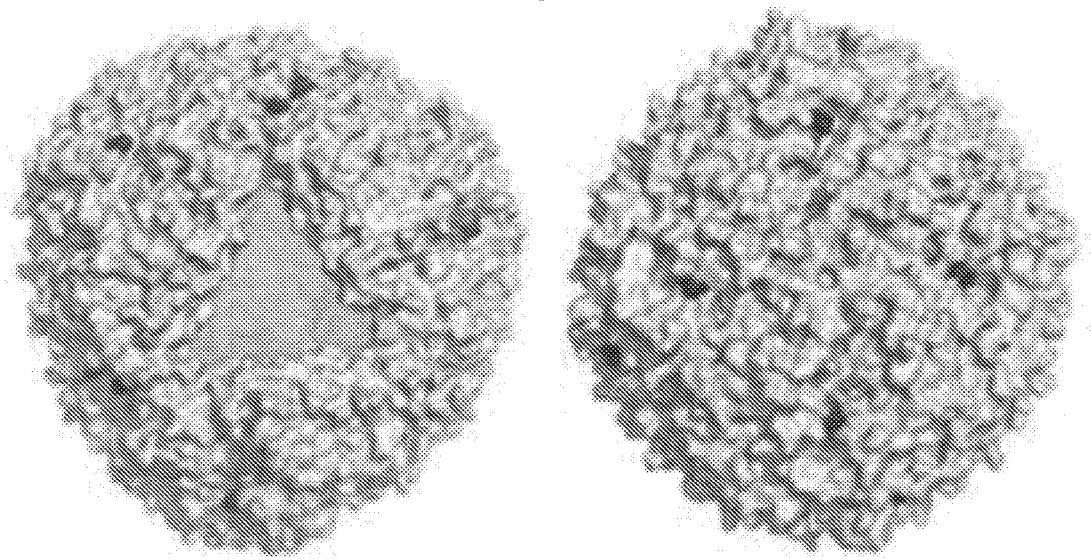

FIG. 5 shows a schematic image of the *Archaeoglobulus fulgidus* ferritin proteins. The N-termini of the individual subunits have been marked in darker shading. Upon successful subunit production and subsequent 24-mer assembly, the attached viral epitopes should be protruding out from the ferritin structure from the N-terminus of each subunit.

Figure 6:
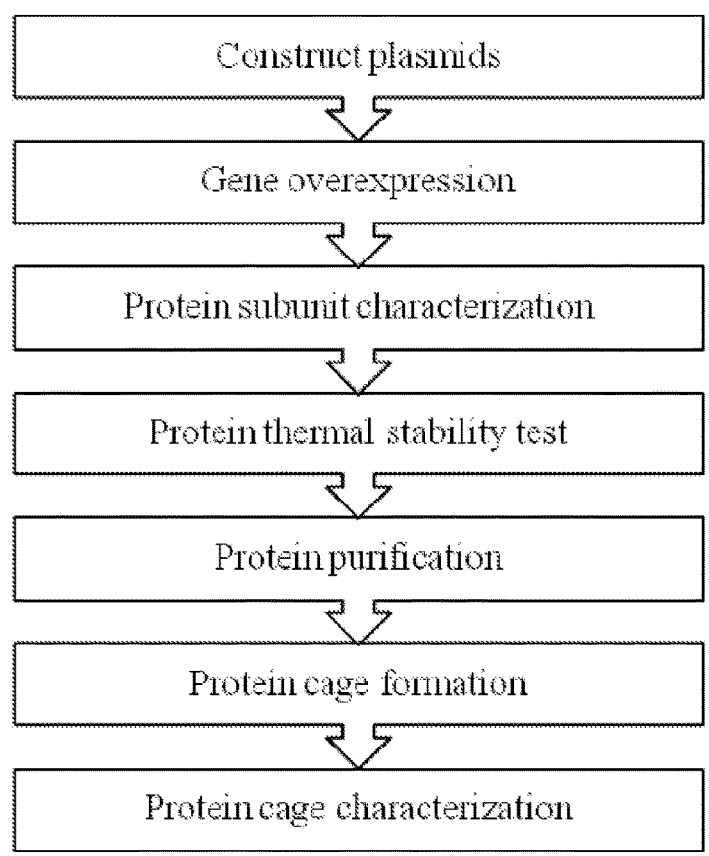

FIG. 6 shows a schematic overview of the experimental procedure for producing the composition as described in the present disclosure.

FIG. 7 shows images of growth of different construct on LB agar plates. (A) shows colony formation of DH5α cells transformed with the pCVAf-IDT plasmid on ampicillin plates. (B) shows colony formation of DH5α cells transformed pCVcAf-IDT plasmid on ampicillin plates. (C) shows colony formation of blank DH5α cells on LB agar without selection antibiotics, showing that the DH5α cells were viable and able to grow on LB agar plates. (D) shows the lack of colony formation of DH5α cells on LB agar plates with ampicillin (negative control).

FIG. 8 shows the comparison of sequencing result (top line; SEQ ID NO: 21) with theoretical DNA (bottom line; SEQ ID NO: 22) sequence of pCVAf after site-directed mutagenesis. The boxed section shows the site where the mutagenesis has occurred.

FIG. 9 shows line graphs depicting growth curves for gene overexpression of pCV-AfFtn-AA and pCVc-AfFtn-AA on pET-11a vector in BL21(DE3)Codon Plus-RIL cells.

FIG. 10 shows a schematic of retaining of hydrophobic biomolecules in a column.

FIG. 11 shows a schematic representation of the theory behind comparing light scattering of larger and smaller particles for dynamic light scattering analysis (DLS).

FIG. 12 shows an image of an SDS-PAGE gel, depicting the results after batch 1 overexpression. A: pCVAf-pET11a/BL21 with IPTG B: pCVcAf-pET11a/BL21 with IPTG C: pCVAf-pET11a/BL21 D: pCVcAf-pET11a/BL21.

FIG. 13 shows a line graph representing a BSA standard curve.

FIG. 14 shows an image of an SDS-PAGE gel, depicting the results of the thermal stability test of batch 1 supernatant.

FIG. 15 shows an image of an SDS-PAGE gel, depicting the results of the thermal stability test of batch 2 samples.

FIG. 16 shows a graph showing the chromatogram of hydrophobic interaction chromatography (HIC) (A) and an image depicting the corresponding SDS-PAGE result (B) for 7 mL CVAf with 0.5 M ammonium sulfate.

FIG. 17 shows a graph showing the chromatogram of hydrophobic interaction chromatography (HIC) (A) and an image depicting the corresponding SDS-PAGE result (B) for 8 mL CVcAf with 0.5 M ammonium sulfate.

FIG. 18 shows a graph showing the chromatogram of hydrophobic interaction chromatography (HIC) (A) and an image depicting the corresponding SDS-PAGE result (B) for 13 mL CVAf with 0.5 M ammonium sulfate.

FIG. 19 shows a graph showing the HIC result (A) and an image depicting the corresponding SDS-PAGE result (B) for 15 mL CVcAf with 1 M ammonium sulfate.

FIG. 20 shows a graph depicting the size distribution for purified CVAf as determined using dynamic light scattering (DLS).

FIG. 21 shows a graph depicting the size distribution for purified CVcAf as determined using dynamic light scattering (DLS).

FIG. 22 shows a sequence alignment comparison for pCVAf-pET-11a (SEQ ID NO: 23 [result] and SEQ ID NO: 24 [theoretical]).

FIG. 23 shows a sequence alignment comparison for pCVcAf-pET-11a SEQ ID NO: 25 [result] and SEQ ID NO: 26 [theoretical]).

FIG. 24 shows an overview of the sequences used herein.

DEFINITIONS

As used herein, the term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

As used herein, the term "nanocapsule" refers to a vesicular system or hollow particle with a shell surrounding a core-forming space, which can be used for transporting a payload on a nanoscale level. A nanocapsule may also be a nano-sized version of a container. The payload of the nanocapsule can be but is not limited to drugs, medicaments, pharmaceutical compositions, chemical compositions, therapeutic compositions, biological macromolecules, dyes, biological material, immunological compositions, nutritional compositions, vitamins, proteins, nucleic acids, antibodies and vaccines. Various materials may be used for producing such nanocapsules. As used herein, the term "nanocage" refers to a nanocapsule, whereby the shell is not solid, as described for the nanocapsule, but has multiple holes or pores in its shell, thereby making it possible for the payload within the core of the nanocage to come into contact with the surrounding environment. These holes or pores may be regular or irregular in shape and/or spacing on the surface of the particle.

As used herein, the term "protein" or "polypeptide" refers to a polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins. The term polypeptide is specifically intended to cover naturally occurring proteins, as well as those that are recombinantly or synthetically produced. Substantially purified polypeptide as used herein refers to a polypeptide that is substantially free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be performed using methods known in the art.

As used herein, the term "fusion protein" refers a protein, or domain (e.g. a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3).

As used herein, the term "self-assembly" refers to a process in which a disordered system of pre-existing components forms an organized structure or pattern as a consequence of specific, local interactions among the components themselves, without external direction. When the constitutive components are molecules, the process is termed molecular self-assembly. Self-assembly can classified as either static or dynamic. In static self-assembly, the ordered state forms as a system approaches equilibrium, reducing its free energy. However, in dynamic self-assembly, patterns of pre-existing components organized by specific local interactions are not commonly described as self-assembled in the art, but are better described as "self-organized".

As used herein, the term "consensus sequence" refers to a sequence of nucleotides found in comparable regions of DNA or RNA, for example in promoter regions (operons) of different genes, in which certain bases occur with a frequency significantly greater than that expected by chance. Although such sequences may vary from case to case, it is possible to derive the most likely sequences overall. One example of a consensus sequence in the Pribnow box of prokaryote promoters. The term "consensus sequence" also applies to sequences of amino acids in polypeptides.

As used herein, the term "sequence identity" refers to the concept that two polynucleotide or amino acid sequences are identical (that is, on a nucleotide-by-nucleotide or residue-by-residue basis or protein-by-protein basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, or at least 90 to 95 percent sequence identity, or at least 99 percent sequence identity as compared to a reference sequence over a comparison window of at least 30 nucleotides (10 amino acids) positions, frequently over a window of at least 24 to 60 nucleotides (8 to 18 amino acids) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the term "vaccine" or "vaccine composition" refers to a composition that can be used to elicit protective immunity in a subject. Thus, after a subject has been vaccinated with an antigen, a vaccine prevents, delays, or lessens the severity of the development of a disease in the subject exposed to the same or a related antigen relative to a non-vaccinated subject. Protective immunity provided by a vaccine can be humoral (antibody-mediated) immunity, or cellular immunity, or both. Vaccination may, for example, eliminate or reduce the load of a pathogen or infected cells, or produce any other measurable alleviation of an infection. Vaccination may also reduce a tumour burden in an immunized (vaccinated) subject. A vaccine can contain any component or components (for example, a vector) that produces an antigen in addition to or in place of an antigen. The terms "vector", "cloning vector", and "expression vector" mean the vehicle by which a nucleic acid sequence (for example, a foreign gene) can be introduced into a host cell, so as to transform the host and promote expression (e.g., transcription and/or translation) of the introduced sequence of an antigen. Vectors include plasmids, phages, and viruses (e.g., a RNA virus such as retroviruses and lentiviruses).

As used herein, the term "mutation" or "variant" refers to changes in a nucleic acid or polypeptide sequences. This term can also include a reference to substantially similar sequences. Generally, nucleic acid sequence mutations of the invention encode a polypeptide which retains qualitative biological activity and/or function in common with the polypeptide encoded by the "non-variant" or "wild type" nucleic acid sequence. Generally, polypeptide sequence mutations of the invention also possess qualitative biological activity and/or function in common with the "non-variant" polypeptide. Further, these mutated polypeptide sequence may have at least 25%, 30%, 35%, 40%, 45%, 50%, 55%, 60%, 65%, 70%, 75%, 80%, 85%, 90%, 95%, 96%, 97%, 98% or 99% sequence identity to the "wild type" polypeptide. Mutants may be made using, for example, the methods of protein engineering and site-directed mutagenesis, as is well known in the art.

In addition to the difference in sequence identity between the mutant or variant amino acid sequences, the variant amino acid sequence should retain the intended function of the non-variant amino acid sequence.

As used herein, the term "immunodominant" refers to epitopes in an antigen that are preferentially recognised by T cells, such that T-cell specific for those epitopes come to dominate the immune response. Therefore, immunodominance is the immunological phenomenon in which immune responses are mounted against only a few of the antigenic peptides out of the many that are produced. That is, despite multiple allelic variations of for example, major histocompatibility complex (MHC) molecules, and other multiple peptides presented on antigen presenting cells, the immune response is skewed to responding to only specific combinations of the two. Immunodominance is evident for both antibody-mediated immunity and cell-mediated immunity. Epitopes that are not targeted or targeted to a lower degree during an immune response are known as subdominant epitopes. The impact of immunodominance is immunodomination, where immunodominant epitopes curtails immune responses against non-dominant epitopes. Antigen-presenting cells, for example dendritic cells, can have up to six different types of MHC molecules for antigen presentation. There is a potential for generation of hundreds to thousands of different peptides from the proteins of pathogens. Yet, the effector cell population that is reactive against the pathogen is dominated by cells that recognize only a certain class of major histocompatibility complex (MHC) bound to only certain pathogen-derived peptides presented by that MHC class. Antigens from a particular pathogen can be of variable immunogenicity, with the antigen that stimulates the strongest response being the immunodominant one. The different levels of immunogenicity amongst antigens forms a concept known as dominance hierarchy.

As used herein, the term "heterosubtypic immunity" refers to the cross-protection that results from an infection with a virus other than the one responsible for the primary infection. For example, influenza A virus serotype may confer cross-protection to a subject when infected with another influenza A virus, other than the one used for primary infection. Therefore, heterosubtypic immunity describes the situation wherein an infection with one virus is able to induce immunity against unrelated sub-strains of the virus.

DETAILED DESCRIPTION OF THE PRESENT INVENTION

Chikungunya virus is a human pathogen and one of the leading causes of mosquito-borne joint pain (arthralgia) in parts of Africa, India and Southeast Asia. Its symptoms include fever, rashes, joint pain, and headache. Since these symptoms are very similar to Dengue fever, Chikungunya is often misdiagnosed as Dengue fever. Although Chikungunya does not result in lethal cases under normal circumstances, the joint pain may last for a prolonged period from several weeks to months, and may become a cause of chronic debilitating pain and contorted posture. Due to lack of specific treatment and licensed vaccine for this disease, there is a critical need for the development of an effective vaccine. The use of protein cage as carrier is done in order to achieve better antigen presentation and immune stimulation in the subject.

The underlying idea of the present invention is an approach for vaccine development by genetically integrating the nucleic acid sequence of the chosen epitope with the nucleic acid sequence of the protein cage, followed by the expression of recombinant nucleic acid sequence (DNA) in an expression system, such as an *Escherichia coli* overexpression system. The advantages of using a protein cage as the epitope carrier include protection of the epitope from premature degradation by innate immunity, control of the pharmacokinetics, as well as improvement on intracellular penetration. Therefore, a novel way of delivering a vaccine displaying a virus epitope, such as the Chikungunya epitope on ferritin protein cage is disclosed. Thus, in one example, the present disclosure describes a composition comprising a viral protein or fragment thereof, wherein the viral protein or fragment thereof is enclosed within a nanocapsule. In one example, nanocapsule formation has formed for a shorter viral protein of 10 amino acids, while for longer viral protein of 18 amino acids, the subunits may not form the correct protein cage, but may aggregate into larger diameter and requires more characterization. Therefore, in one example, the viral protein is between 1 and 18 amino acids long. In another example, the length of the viral protein can be, but is not limited to, about 2 amino acids, about 3 amino acids, about 4 amino acids, about 5 amino acids, about 6 amino acids, about 7 amino acids, about 8 amino acids, about 9 about amino acids, about 10 amino acids, about 11 amino acids, about 12 amino acids, about 13 amino acids, about 14 amino acids, about 15 amino acids, about 16 amino acids or about 17 amino acids. In one example, the viral protein is about 6 amino acids long. In another example, the viral protein is about 18 amino acids long.

The above composition can be used with different epitopes from different viruses. For example, the Togaviridae family is a family of viruses that have a single-strain, positive sense RNA genome. The Togaviridae virus family also belongs to group IV of the Baltimore classification of viruses. This virus family is further divided into two genera, the alphaviruses and the rubiviruses, the difference between the two being that the former's genome is segmented or multipartite, and the genome of the latter is monopartite, which means having a single molecule or strand of nucleic acid. Also, the latter genus currently comprises one representative, namely the rubella virus. Thus, in another example, the composition comprises a viral protein or fragment thereof from a virus of the Togaviridae family. In another example, the viral protein or fragment thereof can be, but is not limited to, an alphavirus. In yet another example, the viral protein or fragment thereof can be, but is not limited to, the Chikungunya virus, the O'nyong'nyong virus, the Semliki Forest virus, the Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and the Ross River virus. In another example, the viral proteins or fragments thereof can be, but is not limited to, the Chikungunya virus, the O'nyong'nyong virus, the Semliki Forest virus, the Sindbis virus and the Ross River virus. In yet another example, the viral protein, or fragment thereof, is from the Chikungunya virus.

As described herein, the novel vaccine platform is designed by displaying virus epitopes, from example the Chikungunya virus, on a protein nanocage comprising of a scaffold protein, for example ferritin. These viral epitopes can be, but are not limited to, immunogenic viral proteins from a virus such as, but not limited to, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus, the Chikungunya virus, the O'nyong'nyong virus, the Semliki Forest virus, the Sindbis virus, and the Ross River virus, which are all representatives of the alphavirus genus of the Togaviridae virus family. In another example, the viral epitopes can be from, but are not limited to the Chikungunya virus, the O'nyong'nyong virus, the Semliki Forest virus, the Sindbis virus, and the Ross River virus. In one example, the present disclosure relates to the use of immunodominant, linear B-cell epitopes of, for example the Chikungunya virus, to induce the production of neutralizing antibodies in a subject upon administration, that is after vaccination. This disclosure further described the development of nanocapsules for presenting immunodominant peptides in a vaccine formulation. Also, the preparation of prophylactic agents for the treatment of a Chikungunya virus infection, as well as other alphaviruses infections is also contemplated.

Figure 2:
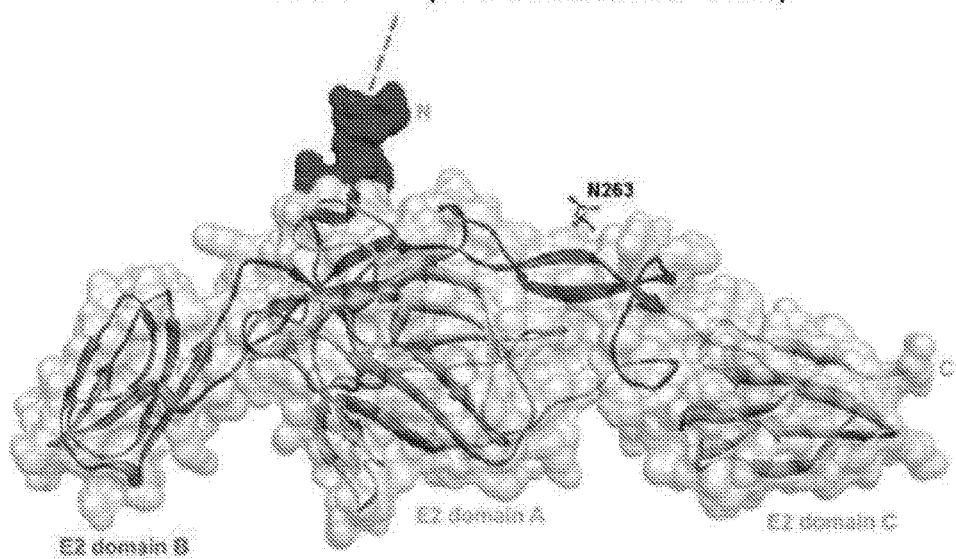
FIG. 2 shows a schematic protein modelling image of the viral Chikungunya glycoprotein E2, showing the spatial orientation of various protein structures, as well as the E2EP3 epitope (SEQ ID NO: 7).
Figure 3:
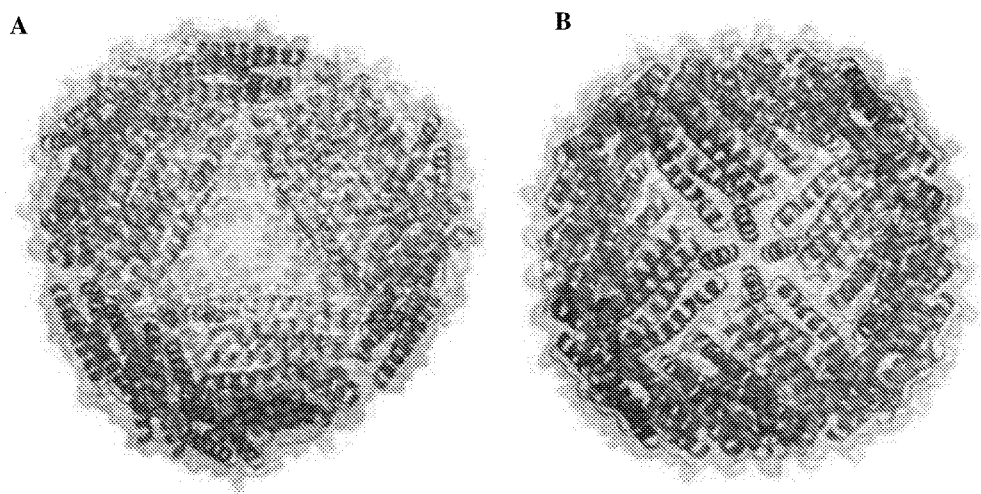
FIG. 3 show a schematic depiction of the quaternary protein structures formed by (A) wild type (AfFtn) and (B)

An epitope is the part of an antigen, the recognition of which results in an immune response by the immune system of the host or subject infected by the pathogen. Therefore, when designing a vaccine or a composition designed to elicit an immune response, one should chose an epitope that is able to elicit as broad an immune response as possible, in order to maximise the immunising potential of the vaccine or composition. For example, by using plasma obtained during the early convalescent phase of Chikungunya-infected patients, it was shown that the early neutralizing IgG3 antibodies dominating the response are mostly specific for a single, linear-shaped epitope. This epitope of these early neutralizing IgG3 antibodies is termed 'E2EP3'(SEQ ID NO: 1), and is located at the N-terminus of the E2 viral glycoprotein, as shown in FIG. 2. Based on further experimental data, it is shown that the core-binding region of E2EP3 (SEQ ID NO: 6) comprises amino acid 3 to 10. It also had been demonstrated that mice vaccinated with the E2EP3 peptide showed reduced viraemia and only minor joint inflammation after the virus challenge, providing further basis for the design of effective vaccines against the Chikungunya virus. For this, C57BL/6 mice were vaccinated with E2EP3 covalently linked to Keyhole limpet hemocyanin (KLH) in the presence of Freund's Adjuvant. Mice were primed and boosted twice with the immunogen (emulsified first with Complete [CFA] and then with Incomplete Freund's Adjuvant [IFA]) over a period of 21 days. Significant anti-E2EP3 titre was detected 19 days post-vaccination after the first boost (data not shown) and was further increased after the second boost at 27 days post-vaccination (data not shown). Importantly, the sera obtained at 27 days post-vaccination were able to neutralize CHIKV-infection in vitro. Compared to the PBS-vaccinated control group, infectivity was reduced by approximately 40% (data not shown). Moreover, virus challenge in mice at 30 days post-vaccination indicated a partial protection by E2EP3 as viremia was reduced from 4500 to 2000 pfu/ml at 2 days post-challenge. This reduction of virus titer was also reflected in clinical symptoms used to monitor the virus-induced inflammation (data not shown). Maximal footpad swelling in the PBS-vaccinated group was more than twice as that of the E2EP3-vaccinated group (data not shown).

As the Chikungunya virus is a representative of the alphavirus genus of the Togaviridae, there is a possibility that hetero-subtypic immunity may occur with the remaining members of the alphavirus genus and the rubivirus genus. Therefore, in one example, the composition is as describe herein, wherein the viral protein, or the fragment thereof, is alphavirus and/or rubivirus. In another example, the composition is as described herein, wherein the alphavirus can be, but is not limited to, Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus. In another example, the composition is as described herein, wherein the alphavirus can be, but is not limited to Chikungunya virus, O'nyong'nyong virus, Semliki Forest virus, Sindbis virus, and Ross River virus. In another example, the alphavirus is Chikungunya virus.

As an example, Chikungunya virus epitopes have been isolated from infected human plasma samples and shown to be linear in nature. It is shown that the genetic fusion of several epitopes, for example, but not limited to, E2EP3 (SEQ ID NO: 1), E2EP4 (SEQ ID NO: 3), E2EP5 (SEQ ID NO: 4), onto the protein nanocage platform does not affect the self-assembly property and morphology of the protein nanocage. Symmetry switching properties of the protein nanocage allows for further spatial control on the displayed epitopes.

As described herein, the full sequence of E2EP3(SEQ ID NO: 1) and the core binding sequence of E2EP3 (SEQ ID NO: 6) are both adopted as Chikungunya virus epitopes. Also utilised in this invention are, for example, the proteins E2EP4 (SEQ ID NO: 3) and E2EP5 (SEQ ID NO: 4). To achieve better protein production in Escherichia coli overexpression system, the nucleic acid sequence of E2EP3 is optimized as shown in Table 2 to be subsequently genetically fused with a scaffold protein, for example ferritin.

TABLE 2

Optimized nucleic acid sequence of the E2EP3 epitope and the core E2EP3 epitope

|  | Amino acid sequence | DNA sequence |
| --- | --- | --- |
| E2EP3 (full sequence) | STKDNFNVYKATRPY LAH (SEQ ID NO: 7) | AGCACCAAAGATAACTTTAA TGTGTACAAA GCAACCCGTCCGTATCTGGC ACAT (SEQ ID NO: 1) |
| Core E2EP3 | STKDNFNVYK (SEQ ID NO: 12) | AGCACCAAAGATAACTTTAA TGTGTACAAA (SEQ ID NO: 6) |

Briefly, in one example, the Chikungunya viral epitope E2EP3 is chosen due to its demonstrated ability to elicit broad immune response. Therefore, in one example, the composition is as described herein, wherein the viral protein or fragment thereof is an epitope of the Chikungunya virus.

In another example, the full epitope (E2EP3; SEQ ID NO: 1) and the core binding sequence of E2EP3 (E2EP3 CV; SEQ ID NO: 6), as well as the proteins E2EP4 (SEQ ID NO: 3) and E2EP5 (SEQ ID NO: 4) are utilised in the present disclosure. Consensus sequences can also be used in the present invention, as these consensus sequences are by definition similar to those of the target epitope and are by virtue of their definition considered to be similar enough to also elicit an immune response when provided to a subject. Therefore, in one example the composition comprises the viral protein or fragment thereof whereby the viral protein or fragment thereof is a consensus sequence to a sequence of, but not limited to E2EP3 (SEQ ID NO: 1), E2EP4 (SEQ ID NO: 3), E2EP5 (SEQ ID NO: 4), and E2EP3 CV (SEQ ID NO: 6).

Furthermore, it is known that proteins of similar identity to that of the target epitope are capable of also eliciting an immune response in a subject, similar to that of the exact sequence of the target epitope. Therefore, in one example the composition is as described herein, wherein the viral protein or fragment thereof has an identity of at least about 70%, about 75%, about 80%, about 85%, about 90%, about 91%, about 92%, about 93%, about 94%, about 95%, about 96%, about 97%, about 98% or about 99% of the viral protein or fragment. In another example, the viral protein or fragment thereof has an identity of 100% of the viral protein or fragment. In one example, the identity as disclosed herein is determined using the nucleic acid sequence. In another example, the identity as described herein is determined using the amino acid sequence.

In light of the above, the difference between proteins can also be described as discreet changes in the sequences, as opposed to percentages of the total sequence. This applies for both the nucleic acid as well as the protein sequence in question. Therefore, in one example, the composition is as described herein, wherein the viral protein or fragment thereof differs by at least 1, at least 2 or at least 3 amino acids from the viral protein or fragment thereof. In another example, the composition is as described herein, wherein the viral protein or fragment thereof can be, but not limited to, the nucleic acid sequences of E2EP3 (SEQ ID NO: 1), E2EP3 mutant (SEQ ID NO: 2), E2EP4 (SEQ ID NO: 3), E2EP5 (SEQ ID NO: 4), E2EP5 mutant (SEQ ID NO: 5), and E2EP3CV (SEQ ID NO: 6). In yet another example, the composition is as described herein, wherein the viral protein or fragment thereof can be, but is not limited to, the protein sequences of E2EP3 (SEQ ID NO: 7), E2EP3 mutant (SEQ ID NO: 8), E2EP4 (SEQ ID NO: 9), E2EP5 (SEQ ID NO: 10), E2EP5 mutant (SEQ ID NO: 11), and E2EP3 CV (SEQ ID NO: 12). In yet another example, the composition is as described herein, wherein the viral protein or fragment thereof can be, but is not limited to, the protein sequences of E2EP3 (SEQ ID NO: 7), E2EP4 (SEQ ID NO: 9), E2EP5 (SEQ ID NO: 10), E2EP3 CV (SEQ ID NO: 12).

As known in the art, vaccines and/or compositions comprising immunogenic proteins or fragments thereof may also include more than one immunogenic protein. Vaccines may comprise one particular antigen or one particular epitope, whereas some include whole deactivated virus, whereby the antigens presented by the deactivated viruses may be of different epitopes and are not necessarily limited to one specific type of protein or epitope. Therefore, the present disclosure also encompasses the use of more than one viral protein in the composition as described herein. Thus, in one example, the composition is as described herein, wherein the nanocapsule comprises viral proteins or fragments thereof of one type only. In another example, the nanocapsule comprises at least 1, 2, 3, 4, 5 or more viral protein(s). In another example, the nanocapsule comprises 2 viral proteins of fragments thereof. In another example, the nanocapsule comprises 3 viral proteins or fragments thereof. In yet another example, the nanocapsule comprises 4 or more viral proteins or fragments thereof.

The existing, widely-used technology in the art of vaccine production consists of the epitope and carrier protein being produced separately and subsequently coupled together. This method of the invention as described herein is, however, a one-step method of producing the whole of the vaccine or the composition. This is done by integrating the epitope(s) with protein cage at a nucleic acid level. This means that the nucleic acid sequence of the epitope is fused with that of a subunit of the protein that comprises the nanocapsule. The expression of this nucleic acid sequence results in a fusion protein comprising the protein epitope and the nanocapsule protein in one construct. Therefore, in one example, the composition is as described herein wherein the viral protein or fragment thereof is attached to a scaffold protein. Therefore, in one example, the present disclosure describes a method of producing the composition as described herein, the method comprising isolating the protein expressed by the vector as described herein, and adding a catalyst in an amount sufficient to catalyse the formation of the nanocapsule.

A linker sequence can be inserted between the viral protein or fragment thereof and the scaffold protein. The insertion of such a linker sequence can have a structural and/or physical effect on the resulting protein, for example reducing potential electrostatic repulsion between the proteins or ameliorating any possible steric effects in the resulting protein chain. Therefore, in one example, the viral protein, or fragment thereof, is attached to the scaffold protein via a linker sequence. The length of the linker sequence is dependent on its function. If it is intended to prevent any steric effects from arising in the resulting protein, then depending on the desired effect to be prevented, a long or short linker sequence would be required. For example, a linker sequence can comprise a single amino acid. A linker sequence can also comprise 2, or 3, or 4, or 5, or 6, or 7, or 8, or 9, or 10, or 15 or more amino acids. A linker sequence can also comprise 2 to 20 amino acids. In one example, the linker sequence comprises 7 amino acids. In another example, the linker sequence comprises 3 amino acids. The amino acids used to make up the linker may be all natural amino acids, or all unnatural amino acids, or combinations thereof. In one example, a linker commonly used is one that follows the format of $(B_xJ_y)_z$, where x, y, z are any integers signifying the number of repeats of the corresponding amino acids or the combination thereof, and whereby B and J represent any natural or non-natural amino acid. In another example, the linker sequence can follow the format of $(G_xS_y)_z$, whereby G is glycine and S is serine. In another example, the placement of G and S in the format $(G_xS_y)_z$ can be interchanged. In one example, x, y and z can independently be an integer between 1 and 20. In one example, x, y and z can be independently 1, 2, 3, 4, 5, 6, 7, 8, 9, 10, 11, 12, 13, 14, 15, 16, 17, 18, 19 or 20. In another example, x can be 1, or 2 or 3. In yet another example, z can be 1 or 2 or 3. In another example, y can be 1 or 2 or 3. In another example, x can be 1 and y can be 3. In yet another example, x can be 1, y can be 3 and z can be 1. In another example, x can be 3, and y can be 1. In yet another example, X can be 1 and y can be 2. In yet another example, x can be 1, y can be 2 and z can be 2. In one example, the linker sequence comprises the amino acids GSSS. In another example, the linker sequence comprises the amino acids GGGS. In a further example, the linker sequence comprises the amino acids GSSGSSG. In another example, the linker sequence comprises the amino acids SGG. In yet another example, the linker sequence is as described herein and is inserted between the viral epitope and ferritin, as an example of a scaffold protein. In yet another example, the linker sequence comprises the amino acids SGG and is inserted between the viral epitope and ferritin, as an example of a scaffold protein.

In the present disclosure, the approach used for producing the viral protein construct is through gene overexpression of the nucleic acid sequence in a microorganism, such as *Escherichia coli* (*E. coli*), whereby the cells of the microorganism are transformed with the recombinant plasmid comprising, for example, the nucleic acid sequence of the viral protein, for example a Chikungunya epitope or fragment thereof, and a scaffold protein, for example ferritin, attached by a linker to the epitope. Using methods known in the art, such as sodium dodecyl sulfate-polyacrylamide gel electrophoresis (SDS-PAGE) as a characterisation tool, it was shown in one example that the expressed protein is successfully produced by the transformed *E. coli* cells and that purification of the protein by hydrophobic interaction chromatography, as known in the art, is successful. Characterization of the protein cage using dynamic light scattering technique as known in the art shows that the protein cage is formed for one of the constructs. Due to its fusion to a scaffold protein as required for the formation of the nanocapsule, the viral protein or epitope is displayed on the N-terminus of each nanocapsule subunit. Instead of expressing the desired viral protein and the scaffold protein separately and subsequently filling the resulting nanocapsule with the desired viral protein, or fusing the scaffold protein directly to the viral protein, the present invention expresses a vector, in which for example the scaffold protein is fused to the viral protein via a linker sequence, thereby expressing one protein construct, which due to the presence of the scaffold protein, will self-assemble into the nanocapsule in the presence of a catalyst.

Nanocapsules carrying peptide sequence can be used in this invention for peptide vaccine presentation and delivery. The nanocapsules can display multiple chikungunya virus epitopes and/or epitopes from other viruses or sub-strains with defined spatial arrangements. The spatial arrangement can be modulated through the symmetry switching of the protein cage. Therefore, in one example, the composition is as described herein, wherein the nanocapsule is a nanocage. In another example, the composition is as described herein, wherein the nanocapsule self-assembles.

The nanocapsules consist of multiple subunits that self-assemble in controlled manner. Each subunit can be attached to a single epitope resulting in a display of multiple epitopes as many as the number of subunits on the nanocapsules. The nanocapsules subunits self-assemble in the presence trace amount of metal (for example, iron) or at high ion concentrations. Therefore, in one example, the catalyst is a metal. In one example, the catalyst is iron or platinum. In another example, the catalyst is a divalent metal. In yet another example, the catalyst is, but is not limited to, $Mn^{2+}$, $Mg^{2+}$, $Co^{2+}$, Pt, $Fe^{3+}$ or $Fe^{2+}$. In another example, the catalyst is $Fe^{3+}$ or $Fe^{2+}$. By taking advantage of the self-assembly property of the nanocapsule, in addition to displaying multiple epitopes of the same type, display of multiple epitopes of different types is also possible. This means that subunits attached to one type of epitope (for example A) can be mixed with other subunits attached to other types of epitope (for example B). Thereby, upon addition of trace amount of metal, the nanocapsule self-assembles and thus displays both A and B on its surface. Therefore, assembly of the nanocapsule can be done using multiple subunits, whereby it is possible that each subunit comprises a different epitope to each other, or that all the subunits comprise the same subunit. It is also possible that a ratio of any kind between at least 1, 2, 3, 4 or more epitopes is utilised in the formation of the nanocapsule. Thus, in one example, the nanocapsule displays epitopes of one type. In another example, the nanocapsule displays different epitopes. In another example, the nanocapsule displays at least two different epitopes. In another example, the nanocapsule displays three or more different epitopes. The types of epitope able to be displayed are as many as the number of subunits that make up the nanocapsule, resulting in a display of multiple epitopes. For example, ferritin, in the presence of iron, is a 24-mer construct, and is therefore made up of 24 subunits. This means that in one example, a ferritin nanocage is able to display 24 different epitopes. Thus, in one example, the nanocapsule displays 24 different epitopes.

Ferritin is a ubiquitous protein produced by almost all living organisms. It has the property of self-assembling into a 24-mer in the presence of iron. *Archaeoglobus fulgidus* wild type ferritin (AfFtn; SEQ ID NO: 15 or 16) can be chosen as the particular type of ferritin used herein due to its hyperthermostability, its unique structure, as shown in FIG. 3, and high structural similarity to human ferritin. Apoferritin is ferritin that is not bound to iron. Therefore, in one example, the composition is as described herein, wherein the nanocapsule is formed by a scaffold protein can be, but is not limited to, the group consisting of ferritin, apoferritin and bacterioferritin. In another example, the scaffold protein is apoferritin. In another example, the scaffold protein is ferritin. In yet another example, the scaffold protein is human ferritin, in another example the scaffold protein is bacterial ferritin. In one example, the composition is as disclosed herein, wherein the scaffold protein is a consensus sequence to a sequence of a wild-type ferritin of SEQ ID NO: 13 (DNA) or SEQ ID NO: 14 (protein). In another example, the scaffold protein is a mutated ferritin protein, wherein at least 1, at least 2, at least 3 or more amino acids differ from the wild-type ferritin of SEQ ID NO: 15 or SEQ ID NO: 16. In yet another example, the mutated ferritin has the sequence according to SEQ ID NO: 13 or SEQ ID NO: 14. In one example, the scaffold protein, as disclosed herein, is a recombinant scaffold protein. In another example, the scaffold protein, as disclosed herein, is isolated from *Archaeoglobulus Fulgidus* (AfFtn). A person skilled in the art would know from which other organisms ferritin can be isolated.

Both wild type ferritin (AfFtn; SEQ ID NOs: 15 or 16) and mutant ferritin (AfFtn-AA; SEQ ID NOs: 13 or 14) ferritins are used as the nanocage as disclosed herein. Wild type ferritin (AfFtn) has a unique tetracosameric structure with 1 triangular opening (~45 Å in diameter) for every 6 subunits, while the mutant version of ferritin (AfFtn-AA) is a mutated protein from the wild type where amino acid residues Lysine at site 150 and Arginine at site 151 were both replaced with Alanine. As a result of mutation, the mutated ferritin (AfFtn-AA) has a closed spherical structure as shown in FIG. 3. Mutations can be made in wild type sequences using site-directed mutagenesis or other mechanisms known in the art. The mutations can be silent mutation, or can be mutations that result in a higher stability of the resulting protein or in a different spatial arrangement of the resulting polypeptide. Mutations are usually performed on the nucleic acid level, with their resulting changes being visible on the protein level.

The unique structure of, for example ferritin (AfFtn), also offers a platform to study the different way of epitope displaying on different shape of protein cages. With two types of epitope and two types of ferritin, there are 4 types of final constructs in this disclosure as shown in Table 3.

TABLE 3

Four types of constructs

| Abbreviations | Full name |
| --- | --- |
| pCVAf-pET-11a | Plasmid of CHIKV epitope-AfFtn in pET-11a |
| pCVcAf-pET-11a | Plasmid of CHIKV core epitope-AfFtn in pET-11a |
| pCVAfAA-pET-11a | Plasmid of CHIKV epitope-AfFtn-AA in pET-11a |
| pCVcAfAA-pET-11a | Plasmid of CHIKV core epitope-AfFtn-AA in pET-11a |

Thus, in the present disclosure, in one example, the composition comprises a nanocapsule and a viral protein or fragment thereof isolated from an alphavirus. In another example, the composition comprises a nanocage and a viral protein or fragment thereof isolated from an alphavirus. In another example, the composition comprises a nanocapsule as described herein and a viral protein or fragment thereof from an alphavirus, wherein the alpha virus is the Chikungunya virus. In yet another example, the composition comprises a nanocage and a viral protein or fragment thereof isolated from an alphavirus. In a further example, the composition comprises a nanocage and a viral protein or fragment isolated from the Chikungunya virus. In one example, the composition comprises a nanocapsule, comprising the scaffold proteins ferritin and a viral protein or fragment thereof isolated from an alphavirus. In another example, the composition comprises a nanocage comprising the scaffold proteins ferritin and a viral protein or fragment thereof isolated from an alphavirus.

The invention, as disclosed herein, also includes the nucleic acid sequences required for the overexpression of the viral protein or fragment thereof and the scaffold protein for the assembly of the nanocapsule. Therefore, in one example, the present disclosure describes a vector comprising the nucleic acid sequence as described herein. In another example, the composition as described herein comprises a vector comprising a gene encoding the viral protein or fragment thereof as described herein, the linker sequence as described herein and the scaffold protein as described herein. The vector as described above is then transformed into a cell for overexpression of the desired proteins, for example into *Escherichia coli* cells. Therefore, the present disclosure refers to an isolated host cell comprising the vector as disclosed herein.

The present disclosure also provides use of the composition in the form of a method of eliciting an immune response in a subject. Therefore, in one example, the present disclosure refers to a method of eliciting an immune response in a subject, the method comprising administering to the subject the composition as described herein. In another example, a vaccine for preventing an infection caused by an alphavirus is provided. Alternatively, in another example, a vaccine is disclosed for preventing an infection caused by an agent, wherein the agent can be, but is not limited to, Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus, the vaccine comprising the composition as described herein. In yet another example, a vaccine for preventing an infection caused by an agent, whereby the agent can be, but is not limited to, Chikungunya virus, O'nyong'nyong virus, Semliki Forest virus, Sindbis virus, and Ross River virus, the vaccine comprising the composition as described herein, is provided. In another example described herein is a method of preventing or ameliorating an infection caused by an alphavirus. In one example, the alphavirus can be, but is not limited to Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus. In another example, the alphavirus can be, but is not limited to, Chikungunya virus, O'nyong'nyong virus, Semliki Forest virus, Sindbis virus and Ross River virus, the method comprising administering to a subject the composition as described herein. In another example, described herein is the use of the composition as described herein for eliciting an immune response in a subject. Also described herein is the use of the composition as described herein for preventing or ameliorating an infection caused by an alphavirus. In one example, the use of the composition as described herein is for preventing or ameliorating an infection caused by, but not limited to, Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus. Also described herein is the use of the composition as described herein for preventing or ameliorating an infection caused by an agent, whereby the agent can be, but is not limited to, Chikungunya virus, O'nyong'nyong virus, Semliki Forest virus, Sindbis virus and Ross River virus.

In this disclosure, nanocapsule technology is employed to develop a peptide-based vaccine against viruses, such as the Chikungunya virus. The method of producing peptide-incorporated nanocapsules, as described herein, would also allow for the design of new therapeutics.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

The experimental procedures for producing the composition as describe herein can be categorized into seven stages as shown in the flowchart in FIG. 6.

Figure 1:
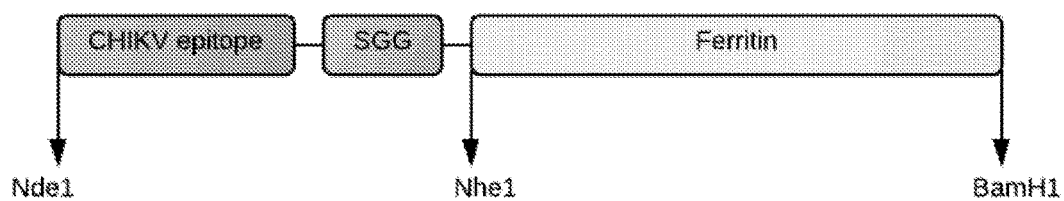
FIG. 1 shows a schematic showing the gene domain arrangement for the Chikungunya virus composition/vaccine, comprising an epitope, for example a CHIKV epitope, a linker sequence, for example SGG and a scaffold protein, for example ferritin. NdeI, NHeI, and BamHI are the restriction sites within or at the end of the sequence.

In the first stage, the plasmids pCVAf-pET11a, pCVcAf-pET11a, pCVAfAA-pET11a, pCVcAfAA-pET11a are constructed and transformed into E. coli DH5α cells for long-term storage, and E. coli BL21-DE3 (C+) RIL cells for gene overexpression. In stage 2 and 3, the protein are produced through gene overexpression and characterized by sodium dodecyl sulfate polyacrylamide gel electrophoresis (SDS-PAGE). In stage 4, the optimal heat treatment conditions, including temperature and duration, are determined. In stage 5, the protein is purified by fast protein liquid chromatography (FPLC). In stage 5, the purified protein subunits undergo iron loading to form protein cage. Finally, the hydrodynamic diameter of the protein cage is measured using dynamic light scattering (DLS), or similar methods as known in the art, while the shape and appearance is visualized by transmission electron microscopy (TEM), or similar methods as known in the art. For the nucleic acid construct design, a gene of interest is inserted in pET-11a for gene overexpression in E. coli system. The DNA composition for CHIKV vaccine is shown in FIG. 1. The enzyme restriction sites NdeI and BamHI are designed to be at the beginning and end so that the gene of interest can be ligated into pET-11a. Nhe1 is inserted between the linker and ferritin so that ferritin can be freely excised as needed.

Complete Plasmid Construct

The amino acid sequence for gene of interest CVAf and CVcAf is as shown in SEQ ID NO: 17 and SEQ ID NO: 18, respectively. The first 3 amino acids, methionine, alanine, serine of the wild type ferritin (AfFtn) were not included because methionine is encoded by start codon, while alanine and serine are the same as the amino acids comprising the Nhe1 restriction site. The approximate molecular weights of CVAf (SEQ ID NO: 19), and CVcAf (SEQ ID NO: 20) are 22.5 kDa, and 21.6 kDa respectively.

Successfully produced the subunits which subsequently assembly correctly to form the 24-mer should display the epitope from the N-terminus of each subunit as highlighted in FIG. 5.

After treating the protein at 75° C. for 15 min, protein purification was performed using fast protein liquid chromatography (FPLC), hydrophobic interaction chromatography (HIC). After multiple attempts of FPLC with different column and different anti-chaotropic salt concentration, as shown in FIGS. 16 (A) and (B), it was established that the optimal purification protocol for CVAf is to use Hitrap (high sub) phenyl FF 1 mL, 0.5M ammonium sulfate, while HiPrep Phenyl FF (high sub) 16/10 with 1 M Ammonium Sulfate should be used for CVcAf as shown in FIGS. 19 (A) and (B).

$FeSO_4$ was loaded into the protein for 24-mer formation at an amount of 500 $Fe^{2+}$ ions per cage. The hydrodynamic diameter of the cage was subsequently measured by Dynamic Light Scattering (DLS). The size distribution result by volume is shown in FIGS. 20 and 21. The wild type ferritin (AfFtn) has an outer diameter of around 12 nm, thus it can concluded that 24-mer has formed for CVcAf (~18 nm), while bigger aggregates have formed for CVAf (~58 nm). It was also determined that the temperature of 75° C. and duration of 15 minutes is the optimal heat treatment condition for CVAf, and CVcAf.

Construction of pCVAf-pET-11a and pCVcAf-pET-11a plasmids-Transformation into DH5α

The two commercial plasmids with wild type ferritin (AfFtn) as protein cage are named pCVAf-IDT and pCVcAf-IDT. After diluting the plasmids to 80 ng/μL, transformation to DH5α competent cells was performed for long-term storage of the plasmids.

Plasmid pCVAf-IDT of 1.5 μl was added to 100 μl thawed competent cells. The mixture was then incubated on ice for 30 min. After heat shock at 42° C. for 45 s, the mixture was incubated on ice for 2 min. Luria-Bertani (LB) broth of 900 μL was added into the mixture for incubation at 37° C. for 45 min. After incubation, transformants of 75 μl were plated onto LB agar plate with ampicillin (100 ng/ml) as selection media to remove the cells that had not taken up the ampicillin-resistant plasmids. The same steps were repeated for the pCVcAf-IDT plasmid. The untransformed competent cells were also plated onto agar plates, one without antibiotics to act as a positive control and one agar plate with antibiotics to act as a negative control, respectively. The agar plates were incubated at 37° C. overnight, and subsequently stored in a 4° C. fridge.

As shown in FIGS. 7 (A) and (B), the colonies were distinct. As for the controls (C) and (D), it can be seen that the colonies grown in plate without antibiotic were all connected together because there is no hindrance in the growing environment, while there were no visible colonies on the ampicillin positive plates containing untransformed DH5α cells, as these cells do not possess antibiotic resistance.

Plasmid Miniprep

For pCVANf-IDT/DH5α/Ampicillin and pCVcAf-IDT/DH5α/Ampicillin constructs, one single colony from the plate was picked and inoculated in 5 mL Luria-Bertani broth with 5 μL ampicillin at 37° C. for overnight culture. Glycerol stocks of pCVAf-IDT/DH5α, and pCVcAf-IDT/DH5α were made with 900 μL Luria-Bertani culture and 600 μL 50% glycerol, which were subsequently stored in −80° C. freezer.

Plasmid extraction from the transformed DH5α cells was then performed using Axygen Axyprep Plasmid Miniprep Kit. The same procedure was repeated for pET-11a/DH5α. The final concentrations of the three plasmids are as follows:

pCVAf-IDT:118.5 ng/μL; pCVcAf-IDT:90.1 ng/μL; and pET-11a:115.6 ng/μL.

Double Digest

After preparing all the plasmids required, the next step is to construct pCVAf-pET-11a, and pCVcAf-pET-11a for gene overexpression in an *Escherichia coli* system. The gene of interest was then cut out from pCVAf-IDT plasmid and pCVcAf-IDT plasmids, and ligated into pET-11a accordingly. Double digestion was performed using Fast Digest Enzyme and Buffer with the detailed reaction mixture shown in Table 4 below.

TABLE 4

20 μL reaction mixture for double digestion

| Samples | Mass of DNA needed (μg) | Sample volume needed (μL) | NdeI enzyme (μL) | BamHI enzyme (μL) | DI water (μL) | Fast Digest Buffer (μL) | Total volume (μL) |
|---|---|---|---|---|---|---|---|
| pCVAf-IDT | 1 | 8 | 1 | 1 | 8 | 2 | 20 |
| pCVcAf-IDT | 1 | 11 | 1 | 1 | 5 | 2 | 20 |
| pET-11a | 1 | 8 | 1 | 1 | 8 | 2 | 20 |

The enzymes were added as the last component to enhance their activity. The mixture was then incubated at 37° C. for 1 hour. Subsequently, 0.8% agarose gel electrophoresis was performed for all the three samples to separate DNA fragments based on their weight. After applying an electric field of 95 V for 32 min, the electrophoresis was completed as indicated by the yellow band that has migrated to ¾ position of the gel. The gel was taken out and immersed in ethidium bromide (EtBr) for 1 hour for DNA staining, and subsequently visualized by UV light. For the samples from the pCVAf-IDT and pCVcAf-IDT plasmids, there were two bands for each of construct, at approximately 2000 bp, and 600 bp, which is the pIDTSmart vector and the gene of interest, that is the combined viral epitope and ferritin, respectively. For the pET-11a construct, there was only one band at 5500 bp, which represents the pET-11a vector without the DNA fragment between NdeI and BamHI restriction sites. The DNA fragment between the NdeI and BamHI restriction sites was not present on the gel because its size is only about 40 bp, while the minimal size to be present on the gel is 250 bp for ThermoScientific GeneRuler 1 kb Ladder.

Gel Extraction

The band at 600 bp for the pCVAf-IDT and pCVcAf-IDT plasmids, and the band at 5500 bp for the pET-11a plasmid were cut out using a sharp blade. Gel extraction was then performed using the QIAquick Gel Extraction Kit to extract the DNA from the gel. The final concentrations of the three DNA fragments are CVAf (insert): 4.9 ng/μL, CVcAf (insert): 7.7 ng/μL and pET-11a (vector): 6.6 ng/μL, respectively.

Ligation

The following step after gel extraction the ligation of the insert into the vector by creating phosphodiester bond between the 3′ hydroxyl of one oligonucleotide of the insert and the 5′ phosphate of the vector. The constructs required for gene overexpression in this disclosure are pCVAf-pET-11a and pCVcAf-pET-11a. Thus, there would be two ligation reactions of "CVAf insert+pET-11a vector" and "CVcAf insert+pET-11a vector". In order to achieve increased ligation efficiency, the optimal amount of insert and vector was calculated as follows. (c—concentration, v—volume, vi—volume of insert, vv—volume of vector)

$$\frac{n_i}{n_v} = 5; n = \frac{c \times v}{\text{number of base pairs}}$$

$$\text{For } pCVAf\text{-}pET11a: \frac{\frac{4.9 \text{ ng/μl} \times v_i}{600}}{\frac{6.6 \text{ ng/μl} \times v_v}{550}} = 5, \frac{v_i}{v_v} \approx 0.4$$

$$\text{For } pCVcAf\text{-}pET11a: \frac{\frac{7.7 \text{ ng/μl} \times v_i}{600}}{\frac{6.6 \text{ ng/μl} \times v_v}{550}} = 5, \frac{v_i}{v_v} \approx 0.6$$

Subsequently, all the reaction ingredients were added as indicated in Table 5.

TABLE 5

10 μL reaction mixture for ligation

| Final plasmids | Volume of insert needed (μL) | Volume of vector needed (μL) | T4 ligase (μL) | 10× T4 buffer (μL) | Total volume (μL) |
|---|---|---|---|---|---|
| pCVAf-pET11a | 2.3 | 5.7 | 1 | 1 | 10 |
| pCVcAf-pET11a | 3 | 5 | 1 | 1 | 10 |

The reaction mixtures were then kept at room temperature for overnight reaction to ensure ample time for ligation. On the next day, the ligates were transformed into DH5α cells and plated on ampicillin agar plate for bacteria selection. After overnight incubation of the agar plates, one single colony from each plate was picked and cultured overnight in 5 mL LB broth with 5 μL ampicillin. Afterwards, glycerol stock of pCVAf-pET-11a/DH5α and pCVcAf-pET-11a/DH5α were made and stored in −80° C. freezer.

To confirm the correctness of DNA sequence of the ligated plasmids, plasmid mini-preparations (mini-preps) were performed for pCVAf-pET11a/DH5α, and pCVcAf-pET11a/DH5α. The plasmid concentration was measured for pCVAf-pET11a at 38.4 ng/μL and for pCVcAf-pET11a at 64.1 ng/μL. The purified plasmids were then sent to 1st Base for DNA sequencing. Comparison between the results of DNA sequencing and theoretical DNA sequence was made and is shown in FIGS. 22 and 23, which show that the ligations were successful.

Construct pCVAfAA-pET-11a and pCVcAfAA-pET-11a

Site-directed mutagenesis is the approach adopted in this project to construct pCVAfAA-pET-11a and pCVcAfAA-pET-11a. The templates used for PCR were pCVAf-IDT, and pCVcAf-IDT. The primers mentioned herein were first diluted to 80 ng/μL with DI water, and the primer mix for PCR is then made by mixing 5 μL forward primer, 5 μL reverse primer, and 15 μL DI water. Reaction mixture for PCR was prepared as shown in Table 6.

In order to mutate the wild type ferritin (AfFtn; SEQ ID NO: 15) into the mutated version of ferritin (AfFtn-AA, K150A, R151A (31 bp); SEQ ID NO: 13), lysine and arginine at amino acid 150, and amino acid 151 are replaced with alanine (codon GCG) using the mutagenesis primers 5' gattggagaggacGCGGCGgctttgctttc 3' (forward; SEQ ID NO: 17) and 5' gaaaagcaaagcCGCCGCgtcctctccaatc 3' (reverse; SEQ ID NO: 18), (melting temperature: 67.3° C., percentage of GC content: 58.1%). This synthetic primer contains the desired mutation GCGGCG and is complementary to the template nucleic acid sequence around the mutation site, thereby being able to hybridize with the denatured template nucleic acid sequence and initiate synthesis. After the single strand mutant is synthesized, the antisense primer binds to the mutant around the mutation site and initiate the synthesis of the complementary strand, thus forming a mutated double-stranded DNA. The basic reaction scheme is shown in FIG. 4.

TABLE 6

50 μL reaction mixture for PCR

| Desired plasmids | Template (μL) | dNTP mix (μL) | Primer mix (μL) | DI water (μL) | pfu buffer + MgSO4 (μL) | pfu DNA poi (μL) | Total volume (μL) |
|---|---|---|---|---|---|---|---|
| pCVAfA-IDT | pCVAf-IDT: 1 | 1 | 2 | 40 | 5 | 1 | 50 |
| pCVcAfA-IDT | pCVcAf-IDT: 1 | 1 | 2 | 40 | 5 | 1 | 50 |

The programmed PCR protocol used for the site-directed mutagenesis is:
Heated lid: 100° C.; Preheat lid: off; Pause: off
In denat 95° C.: 1 minutes—initial denaturation; Hot start: off; Cycles: 30
Seg 95° C.: 30 s—denaturation
52° C.: 30 s—annealing
54° C.: 30 s—annealing
56° C.: 30 s—annealing
58° C.: 30 s—annealing
72° C.: 3 minutes—extension (1000 bp/min)
Fin extn 72° C.: 5 minutes—final extension
Fin hold: 4° C.—final hold As the optimal annealing temperature was unknown, the PCR program above includes four annealing temperatures in order to increase the annealing rate.

After PCR reaction, Dpn1 digestion was carried out to remove the template plasmids. Since the template plasmids were extracted from E. coli, the cytosine or adenine nucleotides of the plasmids are methylated, while the mutant plasmids are unmethylated because they are synthesized by PCR. The enzyme Dpn1 cleaves at methylated site, thereby removing all template plasmids from the reaction and preserving the desired PCR product.

Dpn1 enzyme of 1 μL, and CutSmart buffer of 5 μL were added into 4 μL PCR product, and topped up by 40 μL DI water to a total volume of 50 μL. The mixture was then incubated at 37° C. for 10 min. Subsequently, the Dpn1 digested mixture was transformed into DH5α competent cells, and the transformants were then plated onto Ampicillin agar plate for bacteria selection. On the next day, one single colony from the Ampicillin agar plate was picked out for overnight culture in 5 mL LB broth with 5 μL Ampicillin.

Thereafter, plasmid miniprep was performed and the purified plasmids were sent for sequencing to confirm the correctness of mutant plasmids. From the sequencing results, it can be concluded that pCVcAf-IDT is not mutated, while pCVAf-IDT is successfully mutated as indicated in FIG. 8, extra nucleotides were found in the sequence.

The identity of the extra nucleotides was mixed, with some sections appearing to be from the primers used. It is therefore possible that the primer had annealed to the template multiple times due to the multiple different annealing temperatures.

Gene Overexpression

Competent BL2(DE3)1 C+RIL E. coli cells were transformed with either the pCVAf-pET11a or the pCVcAf-pET11a plasmid and plated on agar plates with ampicillin and chloramphenicol as selection agents. Chloramphenicol was added to confirm the presence of the tRNA-encoding plasmids, so that only cells suitable for protein production would survive. After overnight incubation of the agar plates, one single colony was picked and added into in 5 ml LB broth with ampicillin and chloramphenicol for overnight culture.

Figure 9:
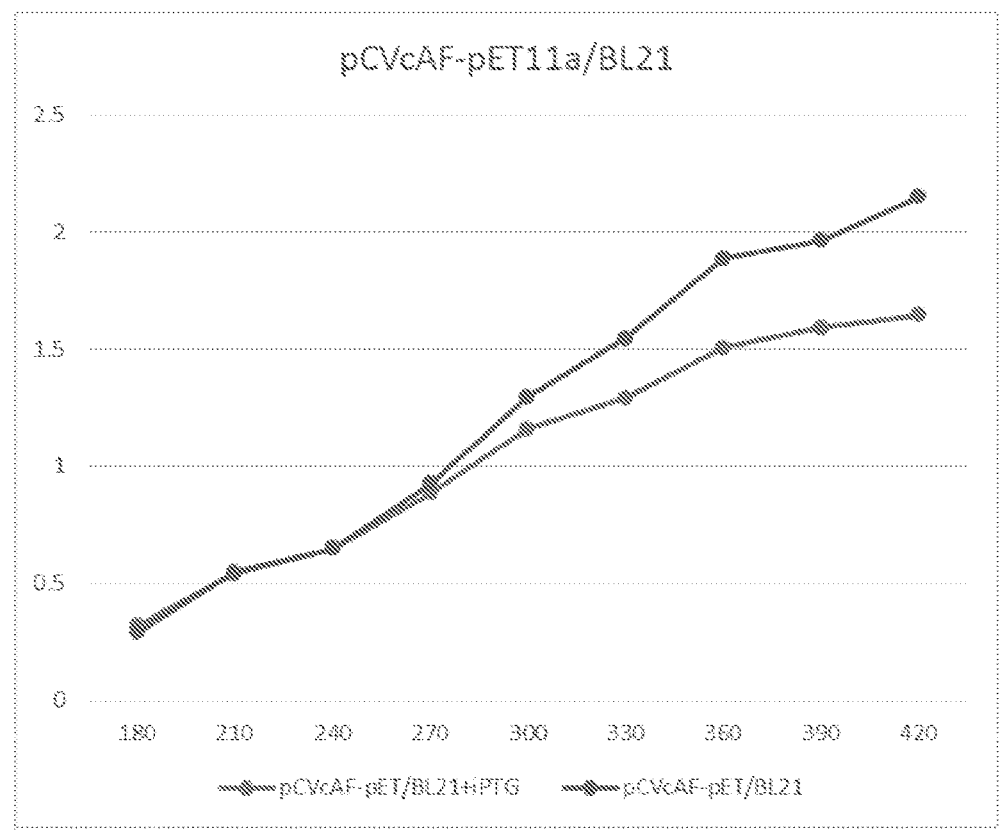

For gene overexpression, four flasks of 100 mL autoclaved Luria-Bertani (LB) broth were prepared. Overnight cultures of 1 mL were added into the autoclaved 100 ml LB Broth for culture at 37° C. After 3 hours, 1 mL of the culture was transferred from the flask and to a cuvette for optical density (OD) measurement at 600 nm wavelength by UV-visible spectrophotometer to monitor the growth condition of E. coli. When the OD reached between 0.6-0.8, Isopropyl β-D-1-thiogalactopyranoside (IPTG) is added into the culture to induce gene overexpression. After another 1 hour (cultured for 4 hours in total), when the OD reached 0.586 for pCVAf-pET11a/BL21, and 0.648 for pCVcAf-pET11a/BL21, IPTG was added to the two flasks to a final concentration of 1 mM and cultured for another 3 hours. The growth curves were plotted in FIG. 9.

Figure 7:
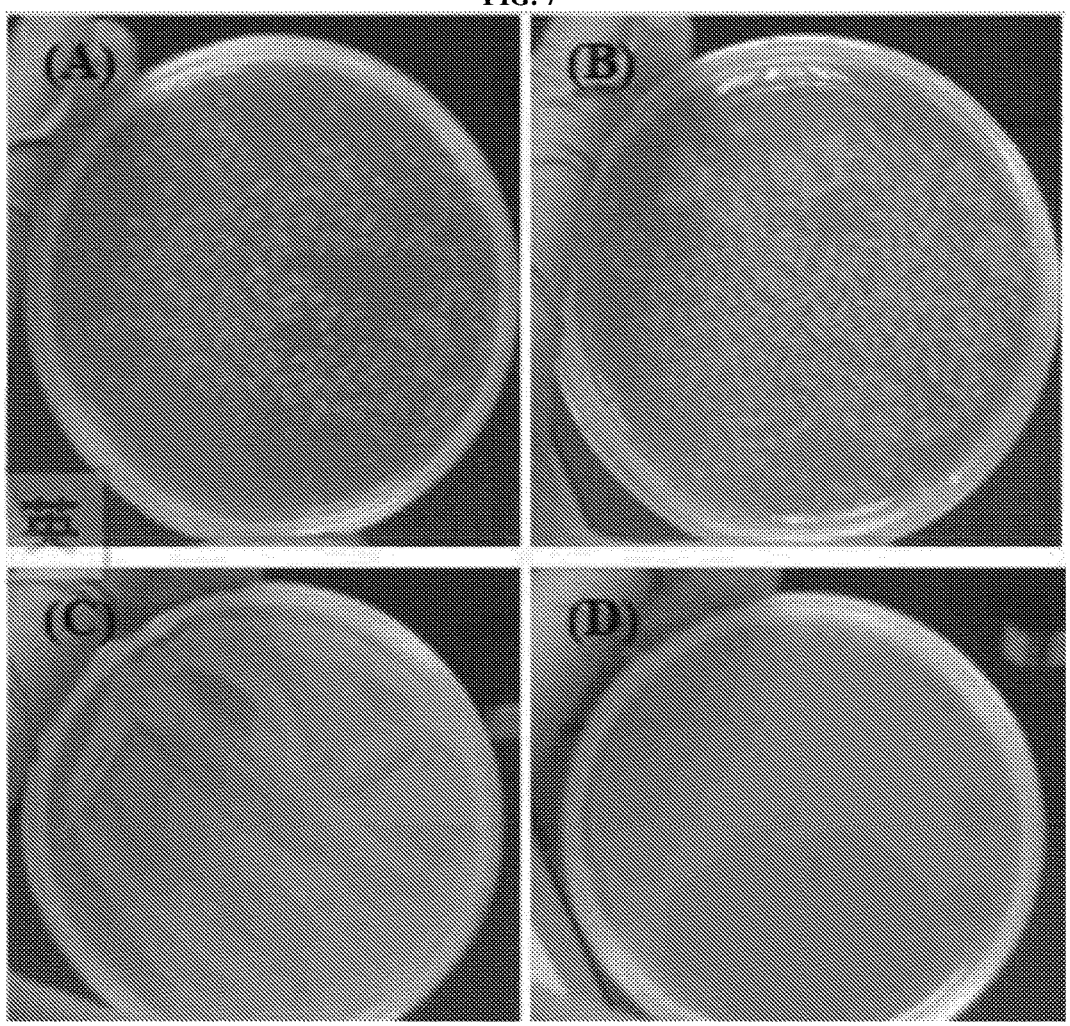

As shown in FIG. 7, the growth of E. coli is slower after the addition of inducer IPTG compared to the flask containing cells to which the inducer was not added. This slowdown in growth of E. coli cells means that the desired fusion protein was being produced. The culture was then harvested by centrifuging at 8,000 g for 15 minutes and the pellets were kept at -20° C.

Protein Subunit Characterization—Protein Extraction

To extract the protein from the cells, the pellets were suspended in 25 mM HEPES, 50 mM Sodium Chloride buffer, pH7.5 (buffer A), by vortexing. After keeping the suspension on ice for 10 minutes to thaw the cells, cell breaking was conducted by sonication at 35% amplitude with 10 s pulse on and 5 s pulse off until the solution was observed to be clear.

Since ferritin has superior thermal stability, heat treatment at 85° C. was conducted for 10 minutes to denature other E. coli proteins. A substantial amount of white precipitate was observed after the heat treatment. The cell debris and precipitated protein were then removed from the solution by centrifuging at 12,000 g for 1 hour at 4° C. At last, the supernatant was transferred to a clean tube and kept at 4° C. During the process, sample of 500 μL from each step (after suspending, after cell breaking, after heat treatment, and supernatant after centrifuging) was taken out for further characterization.

Figure 12:
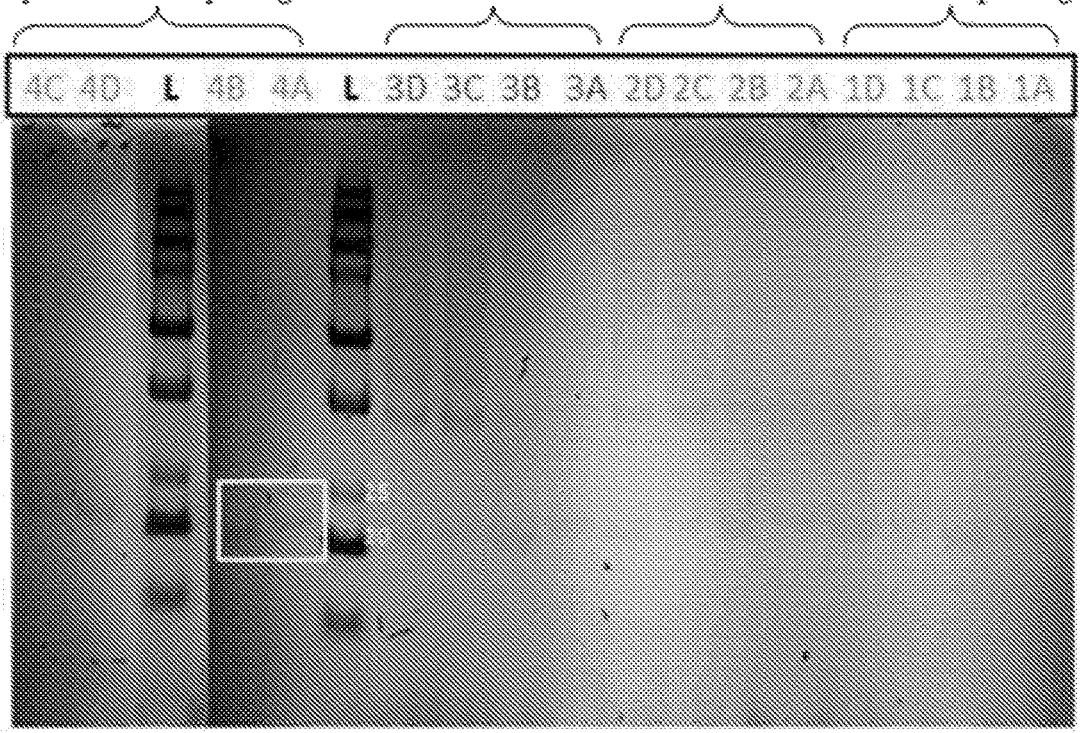

Using the SDS-PAGE experiment described below, or similar methods as known in the art, it was possibly to verify the existence of target protein (molecular weight=21.6 kDa, and 22.5 kDa), as well as the efficiency of heat treatment at 85° C. for 10 min. The result is shown in FIG. 12. As shown in FIG. 12, there were bands for all the samples between 20 kDa and 25 kDa according to the ladder, demonstrating the successful production of target protein. CVAf is slightly heavier than CVcAf, thus it is slightly above the band of CVcAf as framed in the yellow rectangle. Also, for the group of samples after heat treatment, there was only one band present, suggesting that all the *E. coli* proteins were successfully removed by the heat treatment.

Moreover, it can be observed that there is practically no difference of gene overexpression with or without IPTG. The possible causes may be the antibiotics. The presence of both ampicillin and chloramphenicol could be inhibitory to protein production since it is very energy-consuming for bacteria to fight against the antibiotics. As a result, there is not much difference with or without IPTG because the expression is inhibited for both of the two groups. Mostly importantly, group 4 samples only have one band at 20 to 25 kDa, indicating that all other proteins were successfully removed by heat treatment.

Figure 13:
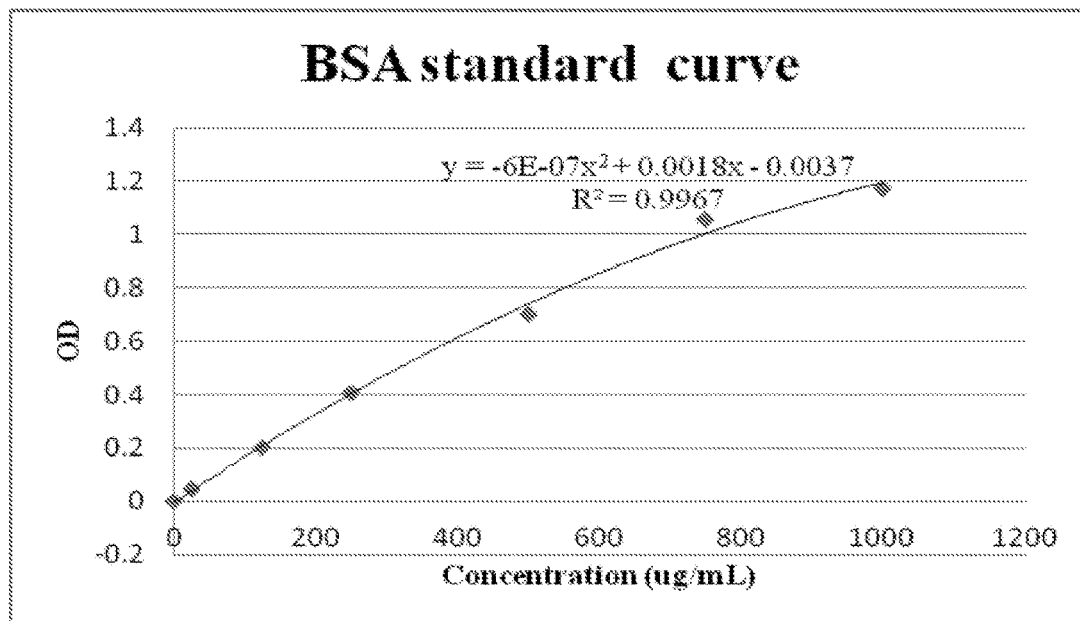

As for the protein concentration measurement, the plotted bovine serum albumin (BSA) standard curve is shown in FIG. 13. From the derived equation, the concentration and yield for the two samples are calculated and shown in table 9.

TABLE 9

Concentration and yield of batch 1 protein

| Protein | Concentration (ug/mL) | Yield for 100 mL culture (mg) |
|---|---|---|
| CVAF | 586 | 5.86 |
| CVcAf | 651 | 6.51 |

Sodium dodecyl sulfate polyacrylaminde gel electrophoresis (SDS-PAGE)

In order to verify the existence of the target protein, SDS-PAGE was performed. However, it is possible to determine the existence of the target protein using other suitable methods as known in the art. The samples were prepared by mixing 7.5 µL of the supernatant and 7.5 µL buffer comprised of 1 fraction β-mercaptoethanol and 19 fractions 2× laemmli sample buffer. The function of buffer is to negatively charge the protein and to mask the native charge of said protein, thereby enabling each protein to migrate in the electrophoretic field in a distance proportional to its molecular weight, and ensure the proteins are present as monomers by breaking any disulfide bonds. The mixture was then heat-treated at 95° C. for 10 minutes, and centrifuged at 10,000 g for 5 minutes.

Subsequently, the samples were loaded into 15-well gel, at 7.5 µL per well. After running at 120 V for 40 minutes, the gels were carefully taken out and washed by DI water three times, and immersed in coomassie blue for staining. After staining for 1 hour on a Bio-shaker, the gels were washed for three times and immersed in DI water for overnight destaining. The gels were visualized under UV light to check the existence of target protein, as well as its purity, after heat treatment.

Bicinchoninic Acid (BCA) Protein Assay

To measure the protein concentration of the supernatant extracted from overexpression induced cells, a bicinchoninic acid assay (BCA) was performed, thereby determining the total protein content of the sample using Thermo Scientific Pierce BCA Protein Assay Kit.

Protein Thermal Stability Test

To study the optimal heat treatment temperature and duration for this overexpressed fusion protein, the first round of thermal stability tests were conducted using the supernatant obtained previously. The different temperatures and durations tested are shown in Table 7.

TABLE 7

Thermal stability test Batch 1 supernatant

| Temperature | Duration: 5 minutes | Duration: 10 minutes | Duration: 15 minutes |
|---|---|---|---|
| 85° C. | CVAF, CVcAf | CVAF, CVcAf | CVAF, CVcAf |
| 95° C. | CVAF, CVcAf | CVAF, CVcAf | CVAF, CVcAf |

After heat treatment, white precipitate was observed to be present in all the samples. After centrifugation at 12,000 g for 30 minutes to remove the precipitate from the solution, the supernatant was removed and transferred to another tube, while the pellet was re-suspended in 200 µL buffer A (25 mM HEPES, 50 mM sodium chloride buffer, pH7.5) and vortexed until it is evenly distributed in the solution. Subsequently, further SDS-PAGE was performed to determine the presence of the target protein in the pellet or supernatant. The samples were kept on ice when not in use during all times for this experiment to ensure its stability.

To further explore the thermal stability of the target protein in a wider range of temperature, another batch of gene overexpression was conducted. Single colony of pCV-cAf-pET11a/BL21, and pCVcAf-pET11a/BL21 were picked from plates and cultured overnight. On the next morning, overnight culture of 1 mL was added into 200 mL LB broth, and cultured in the same way as described previously. This time, 1 mM IPTG was added to both two flasks for gene overexpression.

For cell disruption, the cell pellet was suspended in 15 mL buffer A (25 mM HEPES, 50 mM sodium chloride buffer, pH7.5), and sonicated at 37% Amplitude, 10 s on, and 20 s off until the lysate was clear. Afterwards, the lysate was spun at 8,000 g for 10 minutes to remove the insoluble components and cells debris.

5 mL of supernatant was used for thermal stability test, while the remaining 10 mL was stored for further experimental usage. Heat treatment with the following conditions shown in Table 8 was conducted to find out the optimal temperature and duration to remove unwanted protein while keep most of the target protein.

TABLE 8

Thermal stability test Batch 2 lysate after sonication

| Temperature | Duration: 10 minutes | Duration: 15 minutes | Duration: 20 minutes |
|---|---|---|---|
| 75° C. | CVAf, CVcAf | CVAf, CVcAf | CVAf, CVcAf |
| 80° C. | CVAf, CVcAf | CVAf, CVcAf | CVAf, CVcAf |
| 85° C. | CVAf, CVcAf | CVAf, CVcAf | CVAf, CVcAf |

After the heat treatment, all the samples were centrifuged at 12,000 g for 10 minutes to remove the denatured protein from the solution. The supernatant was removed and transferred to another tube, while the pellet was re-suspended in 100 µL buffer A (25 mM HEPES, 50 mM Sodium Chloride buffer, pH7.5) and vortexed. Subsequently, SDS-PAGE was performed for all the samples.

Thermal Stability Test with Batch 1 Supernatant

Figure 14:
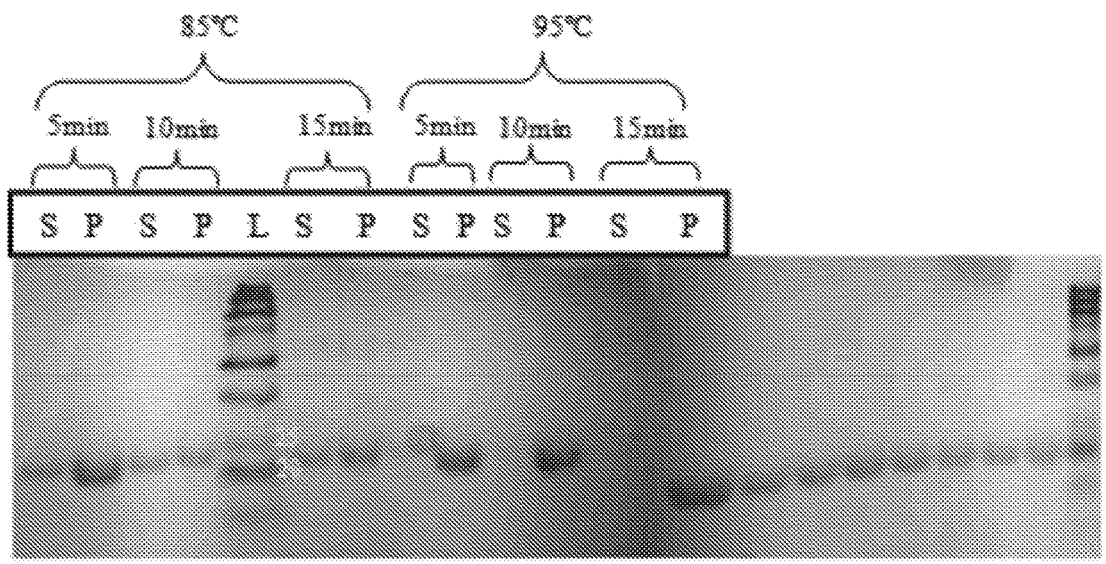

The testing results for sample CVAf is the same as CVcAf, therefore CVAf can be taken as a representative of both. The SDS-PAGE result of supernatant (S) and pellet (P) is shown in FIG. 14. It can be seen that the target protein is present in both the pellet and supernatant for 85° C. heat treatment for all durations, while it is only present in the pellet for 95° C. heat treatment for all durations. Therefore, it can be concluded that part of target protein would be denatured at 85° C., while all the target protein would be denatured at 95° C. Therefore, it is quite definitive that 95° C. is too high to be used as the heat treatment temperature.

Thermal Stability Test with Batch 2 Protein

Figure 15:
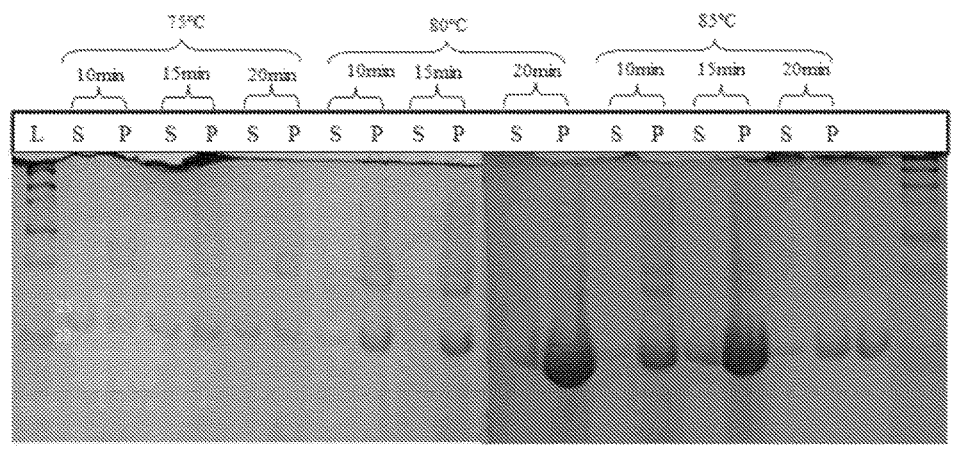

To further explore the optimal heat treatment condition that can retain most of the target protein while remove *E. coli* protein, another test of temperature 75° C., 80° C., and 85° C. was conducted using a new batch that had been sonicated, but had not undergone heat treatment. As can be seen in FIG. 15, the target protein was approximately equally present in the supernatant and pellet when treated at 75° C. according to the band intensity. While at 80° C. and 85° C., most of the target protein was present in the pellet. Therefore the temperature 75° C. is the optimal temperature for heat treatment. Additionally, to ensure that all the *E. coli* protein is removed during the heat treatment, the duration 15 minutes is the chosen to be the optimal. To sum up, the condition of 75° C., 15 minutes was tested to be the standard heat treatment protocol for protein CVAf, and CVcAf.

Protein Purification

Figure 10:
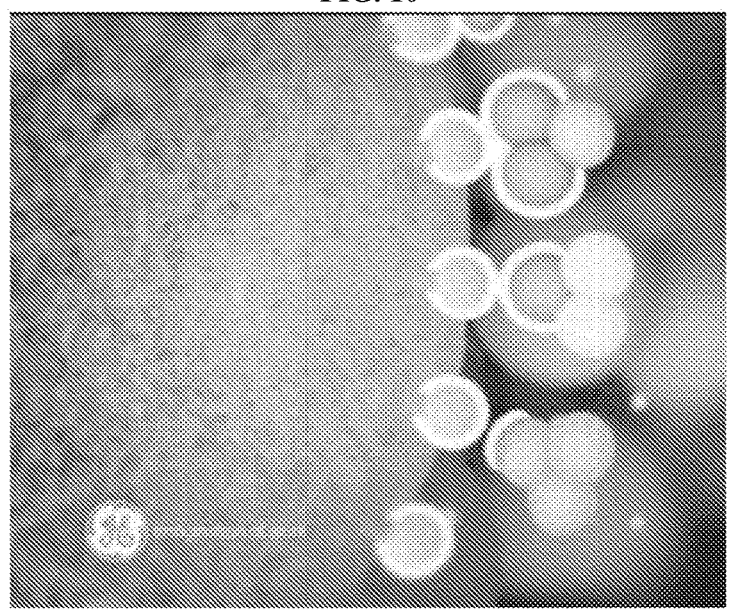

The method chosen for protein purification is known as hydrophobic interaction chromatography (HIC). This purification method relies on the reversible adsorption of biomolecules to the column according to their hydrophobicity. In the presence of anti-chaotropic salt (for example, ammonium sulfate), the hydrophobic component of the biomolecule are induced to be displayed on its surface, resulting in an overall increase in hydrophobicity. The hydrophobic biomolecules then bind to a ligand in the purification column, while the non-hydrophobic biomolecules are eluted out as these do not have the requisite hydrophobicity in order to bind. As a result, the hydrophobic biomolecules are retained on the column, as illustrated in FIG. 10. Subsequently, buffer A without the salt is supplied to the column, resulting in a decrease in hydrophobicity of the bound biomolecules. As a result, the previously retained biomolecules are released from the ligand and be eluted out.

In the present disclosure, the target protein should be the only protein that is not denatured and properly folded after the heat treatment. Therefore, under the influence of ammonium sulfate, the hydrophobic components of the folded target protein are displayed on the surface of the target protein. Other denatured protein or amino acid residues are not able to behave in the same manner due to the disrupted tertiary structure. Thus, the target protein can be separated from other denatured protein or peptides.

Before the experiment, the remaining lysate from the previous experiment was heat-treated with the optimal condition determined from thermal stability tests. After spinning down the lysate for 1 hour at 40,000 g to remove the denatured protein, the samples were ready for purification. Before the experiment, ammonium sulfate was added into the sample to a final concentration of 0.5M. The anti-chaotropic property of ammonium sulfate would promote hydrophobic interactions and increases the adsorption capacity of the HIC later.

The column Hitrap (high sub) phenyl FF 1 mL was installed on the GE ÄKTA FPLC, and equilibrated with 10 mL of 25 mM HEPES, 50 mM Sodium Chloride, 0.5 M ammonium sulfate pH 7.5 (buffer B). Afterwards, CVAf protein of 7 mL was applied to the column with a flow rate of 1 mL/min. The fraction volume is 2 mL, while the gradient length is 10 mL. The procedures were repeated for 8 mL of CVcAf protein.

After the HIC, both the fractions of flow-through and eluent were collected and characterized with SDS-PAGE to check the existence of target protein.

As described above, the unbound protein is expected to be present in the fractions of the first peak, while the target protein should be present in the fractions of the second peak.

Figure 16:
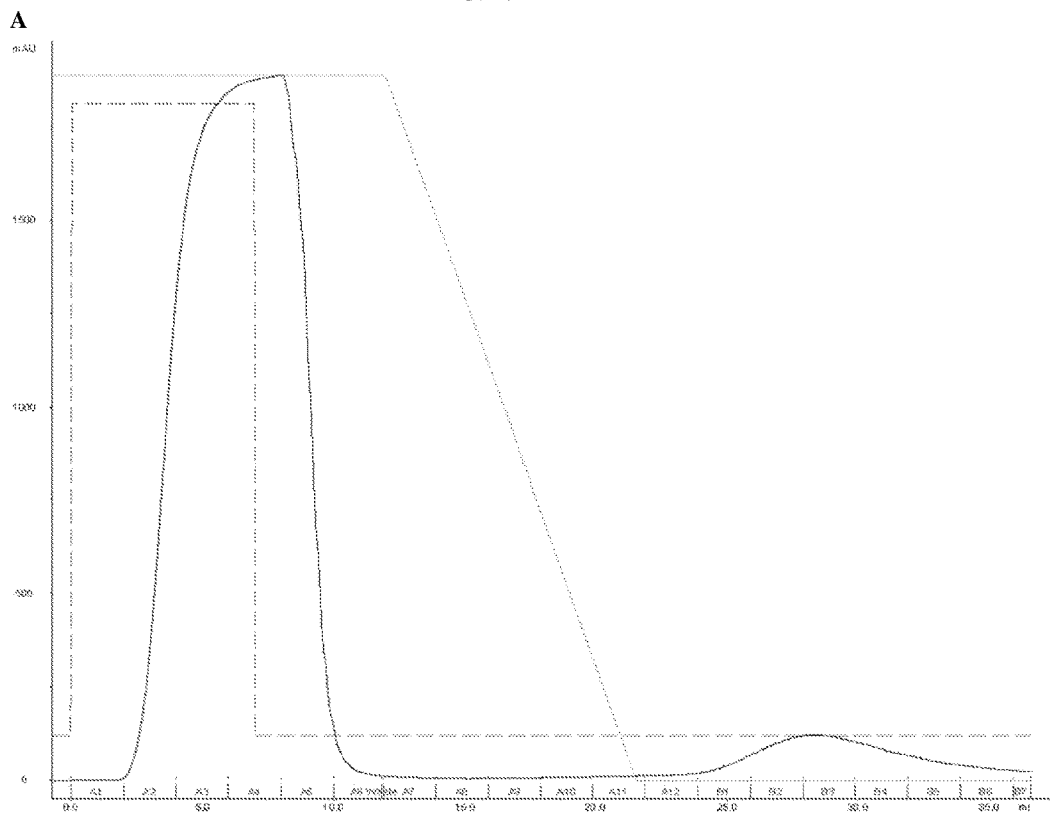
Figure 16:
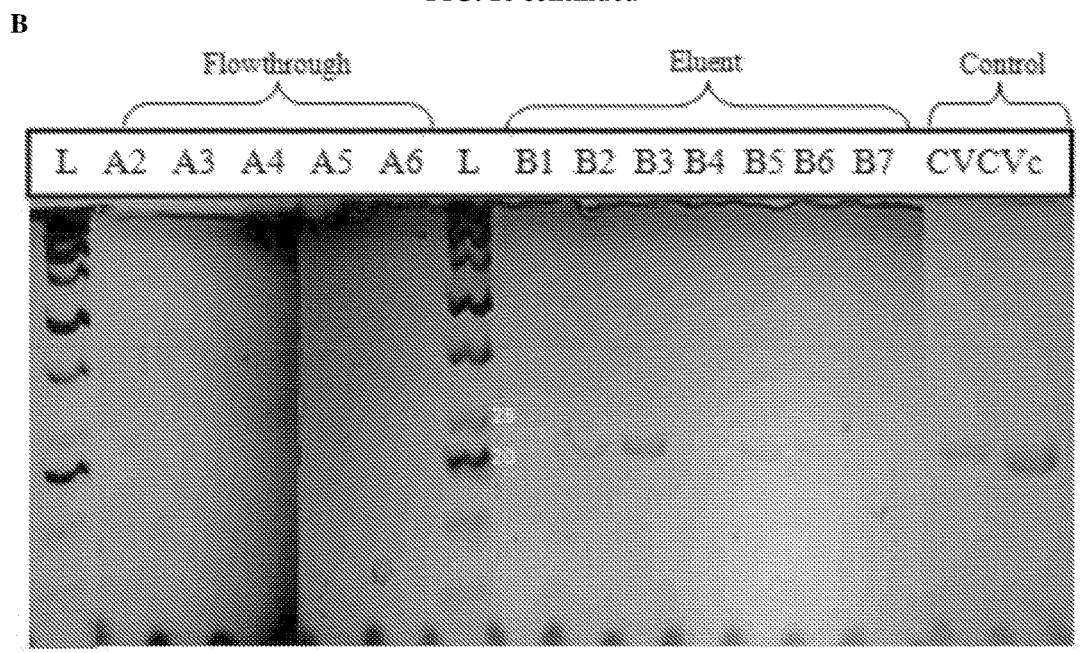

For 7 mL CVAf with 0.5M Ammonium Sulfate, the HIC and SDS-PAGE results are shown in FIG. 16. From the FPLC graph, it can be seen that the fractions for the first peak (flow through) are A2-A6, while the fractions for the second peak (eluent) are B1-B7. As can be seen from the SDS-PAGE result for these fractions, there is no band for all the flow through fractions, while there are bands of the target protein in fractions B2, B3, B5, B6, and B7. Therefore, it can be concluded that this purification method has successfully separated the target protein from impurities such as peptide fragments that cannot be shown on SDS-PAGE.

Figure 17:
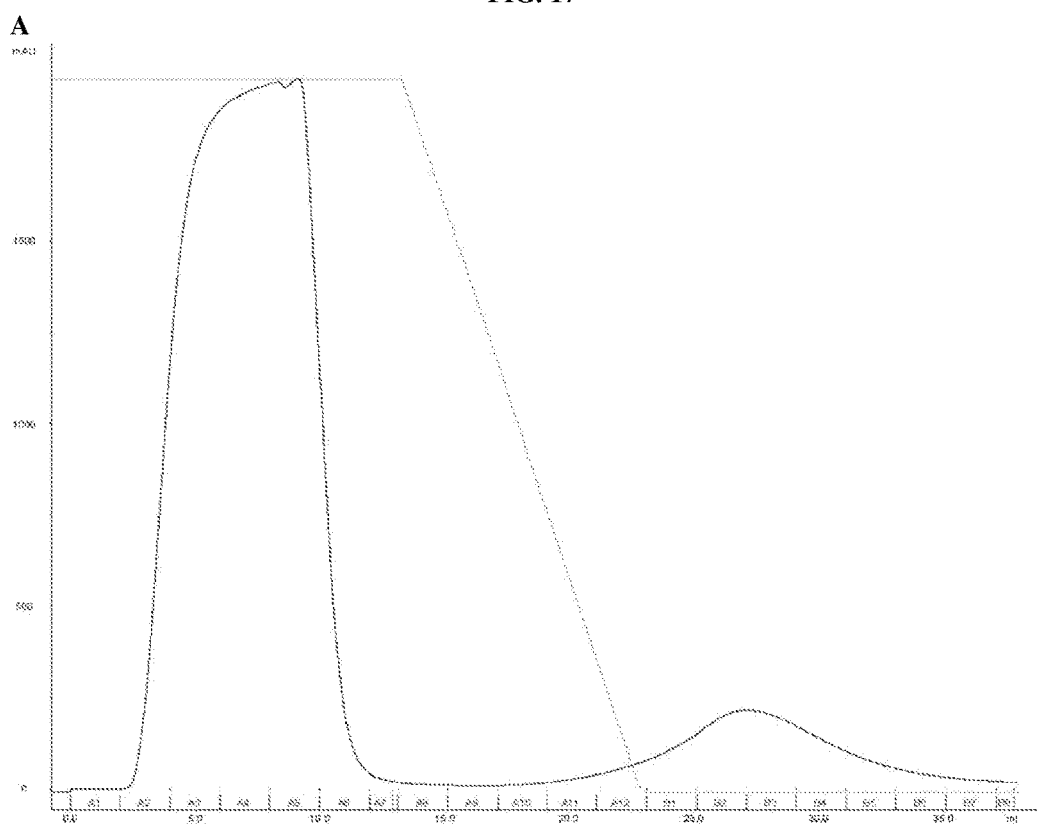
Figure 17:
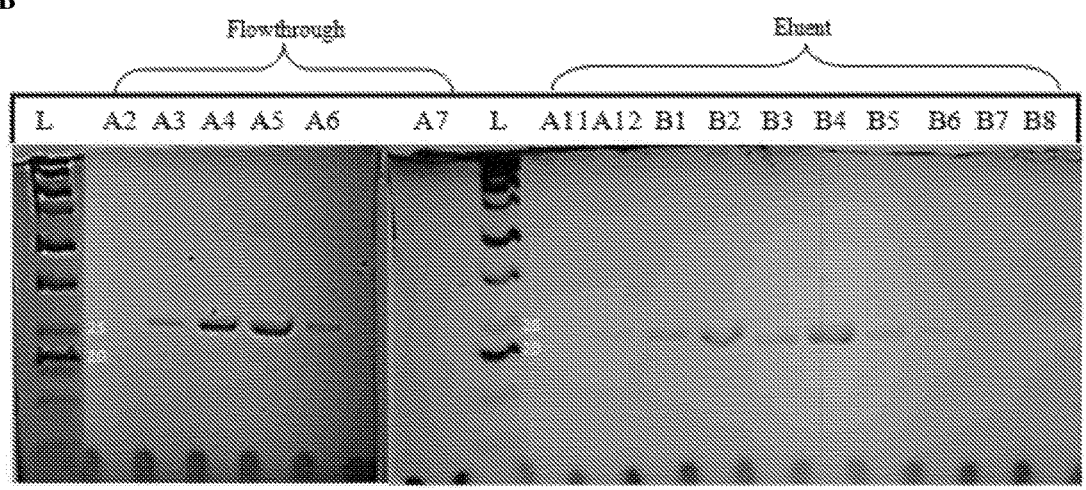

As shown in FIG. 17 for results of sample CVcAf, the eluent peak is slightly higher compared with the CVAF sample, indicating larger amount of protein in the eluent.

Fractions A2-A7 for the first peak, and fractions A11-B8 for the second peak were collected for SDS-PAGE characterization. On the gel picture, bands can be observed for A3, A4, A5, A6 at around 25 kDa. With reference to FIG. 15, which is the SDS-PAGE characterization for thermal stability test, only bands at 20-25 kDa can be observed. Therefore, it can be concluded that this wrong position of the band is due to uneven gel, they are in fact the target protein. Meanwhile, bands between 20 kDa and 25 kDa are present for the eluent fractions A12-B7. Therefore, it can be concluded that part of the target protein is present in the flow through, suggesting that not all of the target protein has bound to the column. This is probably caused by overload of protein into a small column volume.

Fractions of eluent were subsequently pooled for further experimental usage, and the protein concentrations were measured by Thermo Scientific Pierce BCA Protein Assay Kit. For the eluent of CVAf, the concentration was measured to be 0.158 mg/mL, while the concentration for the eluent of CVcAf was 0.212 mg/mL. This is compliant with the fact that the peak of CVcAf is higher than CVAf.

Since the column Hitrap (high sub) phenyl FF 1 mL seems to be too small for CVcAf, another batch of protein (200 mL culture) was produced in order to perform HIC using a bigger column—20 mL HiPrep Phenyl FF (high sub) 16/10 column. In this way, it can be determined whether a bigger volume column can retain all the target protein in the eluent. For the experiment, the fraction volume is set to be 5 mL, and a step function is used instead of a gradient this time.

For CVAf, sample volume of 13 mL was supplied and buffer B with 0.5 M Ammonium Sulfate is used as the start buffer. However, as shown in FIG. 19, there was not evident peak for the elution, so all the flow-through fractions were collected for SDS-PAGE to check the existence of target protein. As shown in the SDS-PAGE result, there was no band for all the fractions in the flow-through. The protein may be present in the eluent, but the peak was not evident due to extremely low concentration.

For the CVcAf sample, the ammonium sulfate concentration was changed to 1 M to see if the change makes any difference. As shown in the HIC result in FIG. 16, there were two peaks B5-B6, and B10-C3 after the supplying of elution buffer. Further characterization of the fractions by SDS-PAGE demonstrated that all the target protein is present at the second elution peak B10-C3.

From the two sets of FPLC experiments using 1 mL and 20 mL column, it can be concluded that an optimal protocol for CVAF purification is to use Hitrap (high sub) phenyl FF 1 mL with 0.5 M Ammonium Sulfate, while an optimal protocol for CVcAf purification is using HiPrep Phenyl FF (high sub) 16/10 column with 1 M Ammonium Sulfate.

Protein Cage Formation—Iron Loading

A ferritin protein cage is formed by 24 ferritin subunits in the presence of irons. In this disclosure, 500 $Fe^{2+}$ ions are loaded for each cage. The required volume of $FeSO_4$ solution was calculated, taken from a stock solution of 0.1M $FeSO_4$ for each sample and added to the purified protein, accordingly. For protein cage formation, the samples were kept in room temperature for 2 hours after addition of the iron ions, and then kept in 4° C. fridge for at least further 12 hours.

With the pooled eluent samples after purification using Hitrap (high sub) phenyl FF 1 mL, iron loading and buffer exchange was performed for protein cage formation and desalting. With the sample volume and measured concentration, the following calculation was performed to obtain the amount of FeSO4 that should be added. For CVAf, molecular weight per cage is: 22.5 kDa×24 subunits≈540 kDa Convert 1 mg/mL to molar: (1÷540,000) M=1.85 µM
0.158 mg/mL CVAF is: 0.158×1.85 µM=0.292 µM
0.292 µM×500=146.22 µM iron needed
The dilution is: 100,000 µM÷146.22 µM=684
Sample volume is 10 mL, so volume of $FeSO_4$ needed is 10 mL÷684=14.62 µL The same calculation was repeated for CVcAf with concentration of 0.212 mg/mL, and volume of 14 mL.

Buffer Exchange

Buffer exchange was performed to the samples that had been previously iron-loaded in order to remove any unbound iron ions. This procedure also removed any peptides that had not formed a protein cage; and also removed any remaining the ammonium sulfate salt that had been added before fast protein liquid chromatography (FPLC). The sample was transferred into a 100 kDa concentrator and centrifuged at 45000 g for 30 seconds at 20° C. Upon completion of the centrifugation, the flow-through was discarded, and the remaining solution was resuspended using pipette. To further concentrate the sample, buffer A (25 mM HEPES, 50 mM Sodium Chloride buffer, pH7.5) was poured into the concentrator for a second purification round. The same procedure was repeated for 3 times. The final retained solution was then transferred to another tube and was increased to a total volume of 1 mL. This solution was centrifuged at 12,000 g for 10 minutes to remove any contamination from the solution prior to further experimental usage.

Protein Cage Characterization—Dynamic Light Scattering

Figure 11:
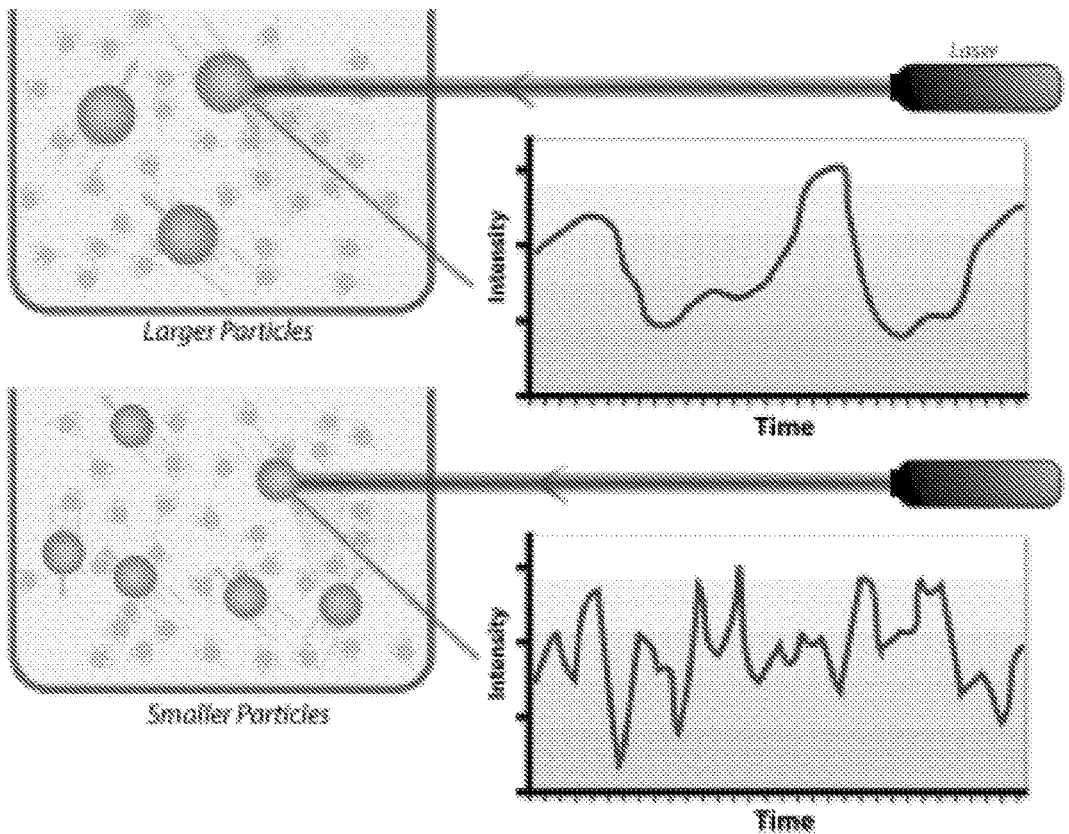

Dynamic light scattering analysis (DLS) was conducted for the samples from the previous section to measure the hydrodynamic diameter of the protein cage. When light hits the particles, it is scattered in all directions as long as the particle size is in the range of 240 nm. Due to Brownian motion, a time-dependent fluctuation in the scattering intensity is to be expected. The larger the particle, the slower fluctuation, as illustrated in FIG. 11. Therefore, the particle hydrodynamic diameter can be deduced based on this correlation with fluctuation rate.

Of 1 mL solution, 700 µL was transferred to a cuvette, which was then put into the Zetasizer machine for measurement. The distribution of hydrodynamic diameter with respect to intensity and volume was obtained using the Zetasizer software. The desired protein cage size was expected to be slightly larger than 12 nm. The smallest size is around 58 nm as showed in FIG. 20. As for sample CVcAf, the smallest size as framed in FIG. 20 is around 18 nm, which is within acceptable range as compared to the outer diameter of AfFtn. The presence of the 58 nm particle for both CVAf and CVcAf was established.

Transmission electron microscopy (TEM)

Since *Archaeoglobus fulgidus* ferritin has an inner and outer diameter of approximately 8 nm to 12 nm, the outer diameter of protein cage displaying the desired epitope don its surface should be slightly bigger than 12 nm. Transmission electron microscopy (TEM) was chosen as the method for visualization, as it is able to image samples in nanoscale size. The samples were diluted to 0.1 mg/mL. After negative staining with uranyl acetate, a drop of sample was placed on a 400-mesh carbon-coated grid and remained to absorb for a minimum of 3 minutes. The grids were placed on 50-ul drop of 1.5% uranyl acetate facing the sample-containing surface towards uranyl acetate solution. The grids were then dried and stored in desiccators before it is observed under the transmission electron microscope. Transmission electron microscopy (TEM) was performed for batch 2 samples after dynamic light scattering (DLS), and nothing was able to be observed. This is most likely caused by premature degradation of the protein since the Transmission electron microscopy (TEM) was performed more than 10 days after iron loading. It may also due to extremely low concentration of protein after buffer exchange. It is recommended that protein purification, cage formation, and TEM be performed within one week in order to avoid unwanted changes in the protein.

---

What is claimed is:

1. A composition comprising a viral protein or fragment thereof, wherein the viral protein, or fragment thereof is enclosed within a nanocapsule, and wherein the viral protein, or fragment thereof is selected from a virus of the Togaviridae family, wherein the nanocapsule is formed by a scaffold protein, wherein the scaffold protein is a mutated ferritin protein encoded by SEQ ID NO. 13 or SEQ ID NO. 14.

2. The composition of claim 1, wherein the viral protein, or the fragment thereof, is selected from the group consisting of alphavirus and Rubivirus.

3. The composition of claim 2, wherein the alphavirus is selected from the group consisting of Chikungunya virus, O'nyong'nyong virus, Semliki Forest virus, Sindbis virus, Aura virus, Babanki virus, Barmah Forest virus, Bebaru virus, Buggy Creek virus, Cabassou virus, Eastern equine encephalitis virus, Everglades virus, Fort Morgan virus, Getah virus, Highlands J virus, Kyzykagach virus, Mayaro virus, Middleburg virus, Mosso das Pedras virus, Mucambo virus, Ndumu virus, Ockelbo virus, Paramana virus, Pixuna virus, Rio Negro virus, Tonate virus, Trocara virus, Sagiyama virus, sleeping disease virus, Salmon pancreatic disease virus, Southern elephant seal virus, Una virus, Venezuelan equine encephalitis virus, Western equine encephalitis virus, Whataroa virus and Ross River virus.

4. The composition of claim 3, wherein the alphavirus is selected from the group consisting of Chikungunya virus, O'nyong'nyong virus, Semliki Forest virus, Sinbis virus, and Ross River virus.

5. The composition of claim 4, wherein the alphavirus is Chikungunya virus.

6. The composition of claim 1, wherein the viral protein or fragment thereof is an epitope of the Chikungunya virus.

7. The composition of claim 1, wherein the viral protein or fragment thereof has an identity of at least about 70%, about 80%, about 90%, about 92%, about 95%, about 97%, about 98% or about 99% of the viral protein or fragment thereof selected from the group consisting of E2EP3 (encoded by SEQ ID NO: 1), E2EP4 (encoded by SEQ ID NO: 3), E2EP5 (encoded by SEQ ID NO: 4), and CV (encoded by SEQ ID NO: 6); or wherein the viral protein or fragment thereof is selected from the group consisting of E2EP3 (encoded by SEQ ID NO: 1), E2EP3 mutant (encoded by SEQ ID NO: 2), E2EP4 (encoded by SEQ ID NO: 3), E2EP5 (encoded by SEQ ID NO: 4), E2EP5 mutant (encoded by SEQ ID NO: 5), and CV (encoded by SEQ ID NO: 6).

8. The composition of claim 1, wherein the viral protein or fragment thereof differs by at least 1, at least 2 or at least 3 amino acids from the viral protein or fragment thereof selected from the group consisting of E2EP3 (SEQ ID NO: 7), E2EP4 (SEQ ID NO: 9), E2EP5 (SEQ ID NO: 10), and CV (SEQ ID NO: 12); or wherein the viral protein or fragment thereof is selected from the group consisting of E2EP3 (SEQ ID NO: 7), E2EP3 mutant (SEQ ID NO: 8) E2EP4 (SEQ ID NO: 9), E2EP5 (SEQ ID NO: 10), E2EP5 mutant (SEQ ID NO: 11), and CV (SEQ ID NO: 12).

9. The composition of claim 1, wherein the nanocapsule comprises viral proteins or fragments thereof of one type only, or wherein the nanocapsule comprises 2, or 3, or 4 or more viral proteins or fragments thereof.

10. The composition of claim 1, wherein the nanocapsule is a nanocage.

11. The composition of claim 1, wherein the scaffold protein is a recombinant scaffold protein.

12. The composition of claim 1, wherein the viral protein or fragment thereof, is attached to the scaffold protein.

13. The composition of claim 12, wherein the viral protein, or fragment thereof, is attached to the scaffold protein via a linker sequence.

14. The composition of claim 13, wherein the linker sequence comprises the amino acids of the format $(G_XS_Y)_Z$; or wherein the linker sequence comprises the amino acids SGG.

15. The composition of claim 1, wherein the nanocapsule self-assembles.

16. A nucleic acid sequence comprising a gene encoding a viral protein or fragment thereof, a linker sequence and a scaffold protein; wherein the viral protein, or fragment thereof is enclosed within a nanocapsule, and wherein the viral protein, or fragment thereof is selected from a virus of the Togaviridae family, wherein the nanocapsule is formed by a scaffold protein, wherein the scaffold protein is a mutated ferritin protein encoded by SEQ ID NO. 13 or SEQ ID NO. 14.

17. A vector comprising the nucleic acid sequence according to claim 16.

18. An isolated host cell comprising the vector according to claim 17.

* * * * *